(12) United States Patent
Townsend et al.

(10) Patent No.: US 6,936,074 B2
(45) Date of Patent: *Aug. 30, 2005

(54) PROSTHETIC FOOT

(76) Inventors: Barry W. Townsend, 400 Houchin Rd., Bakersfield, CA (US) 93304; Byron Kent Claudino, 9731 Rosedale Hwy., Bakersfield, CA (US) 93312

( * ) Notice: Subject to any disclaimer, the term of this patent is extended or adjusted under 35 U.S.C. 154(b) by 0 days.

This patent is subject to a terminal disclaimer.

(21) Appl. No.: 10/790,177

(22) Filed: Mar. 2, 2004

(65) Prior Publication Data
US 2004/0199265 A1 Oct. 7, 2004

Related U.S. Application Data

(63) Continuation of application No. 09/917,660, filed on Jul. 31, 2001, now Pat. No. 6,743,260, which is a continuation-in-part of application No. 09/742,077, filed on Dec. 22, 2000, now Pat. No. 6,443,995.

(51) Int. Cl.[7] .................................................. A61F 2/66
(52) U.S. Cl. ............................. 623/55; 623/52; 623/49
(58) Field of Search .............................. 623/52, 47, 53, 623/49, 46, 50, 55

(56) References Cited

U.S. PATENT DOCUMENTS

| | | | |
|---|---|---|---|
| 951,989 | A | 3/1910 | Hanger |
| 1,013,828 | A | 1/1912 | Thomas |
| 1,071,230 | A | 8/1913 | Hanger |

(Continued)

FOREIGN PATENT DOCUMENTS

| | | |
|---|---|---|
| DE | 179844 | 12/1906 |
| DE | 295807 | 12/1916 |
| DE | 308671 | 10/1918 |

(Continued)

OTHER PUBLICATIONS

*Kinesiology, Scientific Basis of Human Motion*, A The Lever@, pp. 356–361.
AAnkle/Foot Orthoses@, *Orthopedics*, 363–364.
A The AliMed Footdrop Night Split@, *Foot Splints, AFO*, pp. D84–D87.
International Search Report (Jul. 1998); International Application No. PCT/US01/48954.
PCT Written Opinion (Jul. 1998); International Application No. PCT/US02/06901.
International Search Report (Apr. 2002); International Application No. PCT/US02/09571.
International Search Report (Apr. 2002); International Application No. PCT/US02/09573.
International Search Report (Jul. 1998); International Application No. PCT/US02/09589.
International Search Report (Jul. 1998); International Application No. PCT/US02/30471.
International Search Report (Dec. 2003), International Application No. PCT/US03/09506.

*Primary Examiner*—Alvin J. Stewart
(74) *Attorney, Agent, or Firm*—Antonelli, Terry, Stout & Kraus, LLP

(57) ABSTRACT

A prosthetic foot is disclosed for improving the gait and comfort qualities of the amputee that participates in walking, running and jumping activities. An ankle pylon component attached to a foot keel of the foot allows hindfoot triplanar motion. An ankle joint and a subtalar joint provided in the hindfoot ankle pylon component permit closed kinetic chain motion of the foot. The ankle and subtalar joints are formed by respective struts of resilient material of a single piece of material of the ankle pylon component. The ankle pylon component can be used as a functional upgrade component to an existing low profile prosthetic foot, for example.

21 Claims, 14 Drawing Sheets

U.S. PATENT DOCUMENTS

| | | |
|---|---|---|
| 1,128,018 A | 2/1915 | McFarland |
| 1,151,144 A | 8/1915 | Browning |
| 1,294,632 A | 2/1919 | Dickson |
| 1,352,943 A | 9/1920 | Dodge |
| 1,424,264 A | 8/1922 | Shrodes |
| 1,804,915 A | 5/1931 | Collins |
| 2,036,830 A | 4/1936 | Rowley |
| 2,075,583 A | 3/1937 | Lange |
| 2,126,654 A | 8/1938 | Morris |
| 2,197,093 A | 4/1940 | Campbell |
| 2,357,893 A | 9/1944 | Harrington |
| 2,379,538 A | 7/1945 | Meierhofer |
| 2,440,075 A | 4/1948 | Campbell |
| 2,453,969 A | 11/1948 | Carter |
| 2,475,372 A | 7/1949 | Catranis |
| 2,543,908 A | 3/1951 | Guzey |
| 2,556,525 A | 6/1951 | Drennon |
| 2,570,735 A | 10/1951 | Weise |
| 2,605,475 A | 8/1952 | Burger et al. .................. 623/48 |
| 2,619,652 A | 12/1952 | Vesper |
| 2,620,485 A | 12/1952 | Greissinger |
| 2,640,499 A | 6/1953 | Atkins |
| 2,692,392 A | 10/1954 | Bennington et al. |
| 2,699,554 A | 1/1955 | Comelli |
| 2,899,685 A | 8/1959 | Bourcier de Carbon |
| 3,335,428 A | 8/1967 | Gajdos |
| 3,400,408 A | 9/1968 | Garcia |
| 3,438,587 A | 4/1969 | Jackson, Jr. |
| 3,538,516 A | 11/1970 | Bailey et al. |
| 3,707,731 A | 1/1973 | Morgan |
| 3,754,286 A | 8/1973 | Ryan |
| 3,833,941 A | 9/1974 | Wagner |
| 3,874,004 A | 4/1975 | May |
| 3,889,301 A | 6/1975 | Bonner, Sr. |
| 3,890,650 A | 6/1975 | Prahl |
| 3,953,900 A | 5/1976 | Thompson |
| 4,007,496 A | 2/1977 | Glabiszewski |
| 4,089,072 A | 5/1978 | Glabiszewski |
| 4,091,472 A | 5/1978 | Daher et al. |
| 4,128,903 A | 12/1978 | Marsh et al. |
| 4,161,042 A | 7/1979 | Cottingham et al. |
| 4,177,525 A | 12/1979 | Arbogast et al. |
| 4,180,872 A | 1/1980 | Chaikin |
| 4,225,982 A | 10/1980 | Cochrane et al. |
| 4,268,922 A | 5/1981 | Marsh et al. |
| 4,302,856 A | 12/1981 | May |
| 4,306,320 A | 12/1981 | Delp |
| 4,314,398 A | 2/1982 | Pettersson |
| 4,328,594 A | 5/1982 | Campbell et al. |
| 4,360,931 A | 11/1982 | Hampton |
| 4,370,761 A | 2/1983 | Serri |
| 4,395,783 A | 8/1983 | Eyre et al. |
| 4,397,048 A | 8/1983 | Brown et al. |
| 4,459,709 A | 7/1984 | Leal et al. |
| 4,506,395 A | 3/1985 | Haüpt |
| 4,619,661 A | 10/1986 | Axelsson |
| 4,636,220 A | 1/1987 | Ziegelmeyer |
| 4,645,509 A | 2/1987 | Poggi et al. |
| 4,652,266 A | 3/1987 | Truesdell |
| 4,676,800 A | 6/1987 | Chen |
| 4,721,510 A | 1/1988 | Cooper et al. |
| 4,792,340 A | 12/1988 | Aulie et al. |
| 4,822,363 A | 4/1989 | Phillips |
| 4,865,612 A | 9/1989 | Arbogast et al. |
| 4,883,493 A | 11/1989 | Martel et al. |
| 4,892,553 A | 1/1990 | Prahl |
| 4,892,554 A | 1/1990 | Robinson |
| 4,911,724 A | 3/1990 | Fikes |
| 4,923,475 A | 5/1990 | Gosthnian et al. |
| 4,938,776 A | 7/1990 | Masinter |
| 4,938,777 A | 7/1990 | Mason et al. |
| 4,959,073 A | 9/1990 | Merlette |
| 4,994,086 A | 2/1991 | Edwards |
| 5,004,477 A | 4/1991 | Palfray |
| 5,007,938 A | 4/1991 | Prahl |
| 5,019,109 A | 5/1991 | Volsin |
| 5,037,444 A | 8/1991 | Phillips |
| 5,062,859 A | 11/1991 | Naeder |
| 5,066,305 A | 11/1991 | Firth |
| 5,071,435 A | 12/1991 | Fuchs et al. |
| 5,108,454 A | 4/1992 | Rothschild et al. |
| 5,112,356 A | 5/1992 | Harris et al. |
| 5,116,381 A | 5/1992 | Palfray |
| 5,116,384 A | 5/1992 | Wilson et al. |
| 5,116,385 A | 5/1992 | Allard et al. |
| 5,156,631 A | 10/1992 | Merlette |
| 5,156,632 A | 10/1992 | Wellershaus |
| 5,158,570 A | 10/1992 | Schey et al. |
| 5,181,932 A | 1/1993 | Phillips |
| 5,219,364 A | 6/1993 | Lloyd |
| 5,219,365 A | 6/1993 | Sabolich |
| 5,258,038 A | 11/1993 | Robinson et al. |
| 5,314,499 A | 5/1994 | Collier, Jr. |
| 5,336,270 A | 8/1994 | Lloyd |
| 5,367,790 A | 11/1994 | Gamow et al. |
| 5,376,133 A | 12/1994 | Gramnas |
| 5,376,139 A | 12/1994 | Pitkin .......................... 623/51 |
| 5,376,140 A | 12/1994 | Ryan |
| 5,376,141 A | 12/1994 | Phillips |
| 5,425,781 A | 6/1995 | Allard et al. |
| 5,443,522 A | 8/1995 | Hiemisch ..................... 623/49 |
| 5,443,527 A | 8/1995 | Wilson |
| 5,458,656 A | 10/1995 | Phillips |
| 5,486,209 A | 1/1996 | Phillips |
| 5,507,838 A | 4/1996 | Chen |
| 5,509,937 A | 4/1996 | Allard et al. ................. 623/55 |
| 5,514,185 A | 5/1996 | Phillips |
| 5,547,913 A | 8/1996 | Muramoto |
| 5,549,714 A | 8/1996 | Phillips |
| 5,571,212 A | 11/1996 | Cornelius ..................... 623/48 |
| 5,593,457 A | 1/1997 | Phillips |
| 5,653,767 A | 8/1997 | Allen et al. |
| 5,653,768 A | 8/1997 | Kania |
| 5,695,526 A | 12/1997 | Wilson |
| 5,695,527 A | 12/1997 | Allen |
| 5,746,773 A | 5/1998 | Littig |
| 5,766,264 A | 6/1998 | Lundt .......................... 623/47 |
| 5,769,896 A | 6/1998 | Rosendahl et al. |
| 5,776,205 A | 7/1998 | Phillips |
| 5,800,568 A | 9/1998 | Atkinson et al. |
| 5,800,569 A | 9/1998 | Phillips |
| 5,824,112 A | 10/1998 | Phillips |
| 5,897,594 A | 4/1999 | Martin et al. |
| 5,899,944 A | 5/1999 | Phillips |
| 5,913,901 A | 6/1999 | Lacroix ....................... 623/47 |
| 5,944,760 A | 8/1999 | Christensen |
| 5,976,191 A | 11/1999 | Phillips |
| 5,993,487 A | 11/1999 | Skardoutos et al. |
| 5,993,488 A | 11/1999 | Phillips |
| 6,099,572 A | 8/2000 | Mosler et al. |
| 6,129,766 A | 10/2000 | Johnson et al. ............... 623/49 |
| 6,187,052 B1 | 2/2001 | Molino et al. |
| 6,197,066 B1 * | 3/2001 | Gabourie ..................... 623/52 |
| 6,206,934 B1 | 3/2001 | Phillips |
| 6,228,043 B1 | 5/2001 | Townsend et al. |
| 6,270,468 B1 | 8/2001 | Townsend et al. |
| 6,402,790 B1 | 6/2002 | Celebi |
| 6,443,995 B1 * | 9/2002 | Townsend et al. ............ 623/55 |
| 6,562,075 B2 | 5/2003 | Townsend et al. |
| 6,692,454 B1 | 2/2004 | Townsend et al. |
| 6,743,260 B2 * | 6/2004 | Townsend et al. ............ 623/52 |

FOREIGN PATENT DOCUMENTS

| | | |
|---|---|---|
| DE | 325171 | 9/1920 |
| DE | 325171 C1 | 10/1920 |
| DE | 379849 | 8/1923 |
| DE | 389252 | 2/1924 |
| DE | 306313 | 2/1929 |
| DE | 807214 | 7/1949 |
| DE | 883331 | 7/1949 |
| DE | 963849 | 5/1957 |
| DE | 1179328 | 10/1964 |
| DE | 1211354 | 2/1966 |
| DE | 2241971 | 8/1972 |
| DE | 27 18 395 | 11/1977 |
| DK | 0 648 479 A1 | 10/1993 |
| GB | 22172 | of 1898 |
| GB | 120445 | 11/1918 |
| GB | 120462 | 11/1918 |
| GB | 275902 | 8/1927 |
| GB | 306313 | 4/1928 |
| GB | 621576 | 4/1949 |
| GB | 1371996 | 5/1973 |
| GB | 1432481 | 5/1974 |
| GB | 2092451 | 8/1982 |
| GB | 2124493 | 2/1984 |
| GB | 2202448 | 9/1988 |
| SE | 445515 | 6/1986 |
| SU | 605613 | 4/1978 |
| SU | 778732 | 12/1980 |
| SU | 806023 | 2/1981 |
| SU | 997204 | 2/1983 |
| SU | 1465045 | 3/1989 |
| SU | 1465046 | 3/1989 |
| SU | 1477401 | 5/1989 |
| SU | 1488490 | 6/1989 |
| SU | 1600759 | 10/1990 |
| WO | 88/00815 | 2/1988 |
| WO | 89/05617 | 6/1989 |
| WO | 89/09036 | 10/1989 |
| WO | WO 94/10942 | 5/1994 |

\* cited by examiner

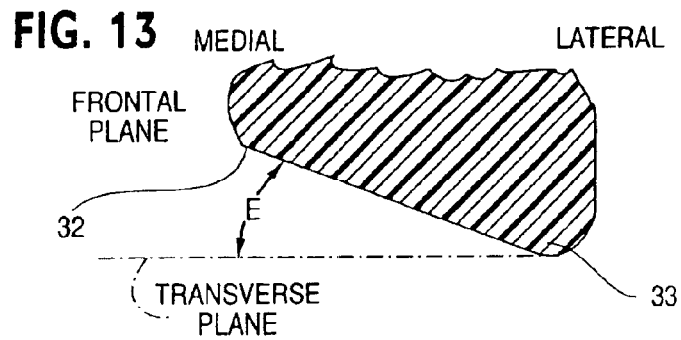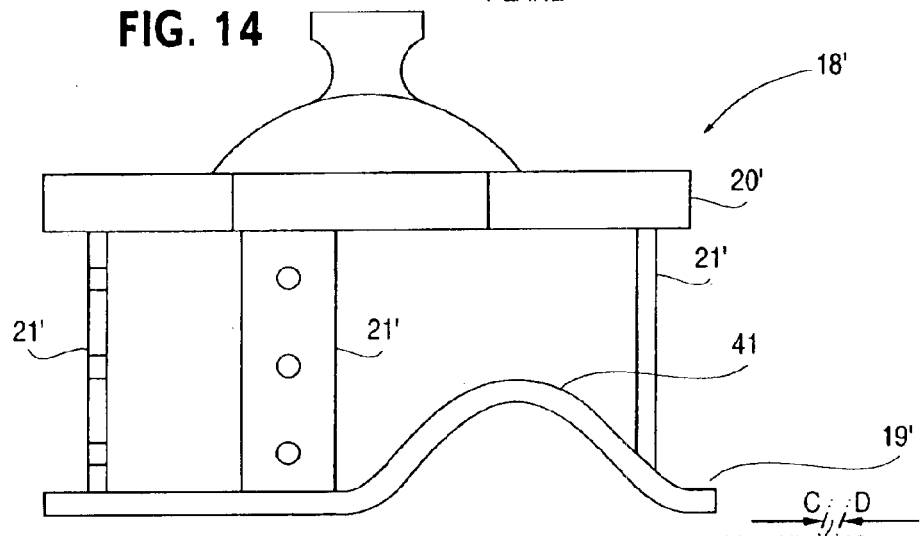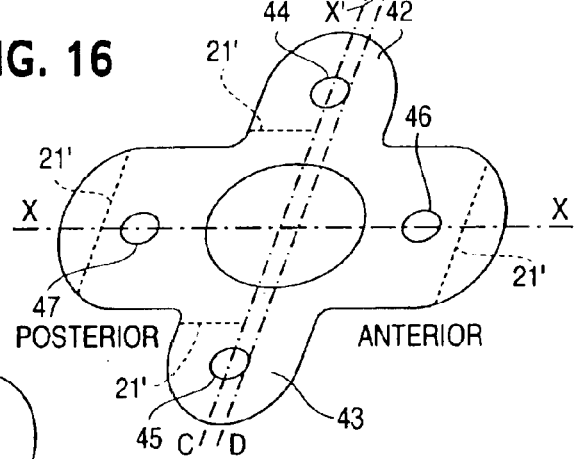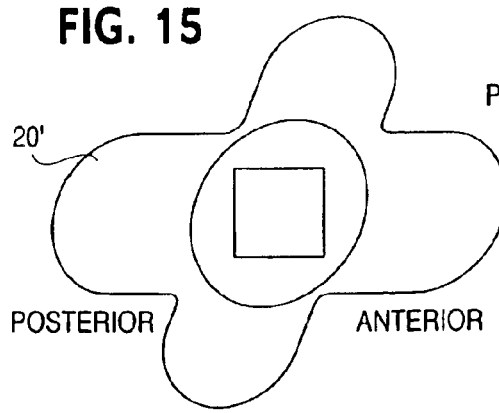

PROSTHETIC FOOT

RELATED APPLICATIONS

This application is a continuation of application Ser. No. 09/917,660, filed Jul. 31, 2001, now U.S. Pat. No. 6,743,260 issued Jun. 10, 2004, which is a continuation-in-part of application Ser. No. 09/742,077, filed Dec. 22, 2000, now U.S. Pat. No. 6,443,995, issued Sep. 3, 2002, the disclosure of which is hereby incorporated by reference.

TECHNICAL FIELD

A prosthetic foot that mimics the human foot in function is disclosed. The prosthetic foot has hindfoot triplanar motion capability, biplanar midfoot and forefoot motion capabilities and high low dynamic response characteristics for improving gait and comfort qualities of the amputee in walking, running and jumping activities. An ankle pylon component providing hindfoot triplanar motion capability for upgrading an existing low profile prosthetic foot is also disclosed.

BACKGROUND AND SUMMARY

Those in the field of prosthetics have in the past manufactured prosthetic feet which permit varying degrees of motion capability. Most of the known prosthetic feet utilize metal hinges with rubber bumpers to enable this motion capability. These components are sources for mechanical failures and wear. The known prosthetic feet are also generally expensive to produce and maintain. None of the conventional prosthetic feet mimic human gait characteristics, e.g., while known designs allow some motion capability, the conventional prosthetic feet do not reflect humanoid characteristics. These characteristics relate to the biomechanical function of the human foot and ankle joint in gait. The prior art prosthetic feet have not achieved true human gait characteristics because their design features do not mimic the human foot.

The human foot is a complex comprised of twenty-six separate bones. The bones of the foot articulate with one another to create joints. The joints of the foot, through these articulations, allow movement to occur. The motion capability of a particular joint is dependent upon bony articulations, ligamentous reinforcements and muscular control. Motion capability of specific joints of the foot has been studied quite extensively through history. These scientific studies have identified fourteen different axes of rotations of all the joints of the human foot. They have through thoughtful analysis determined how these axes of rotations and motion capabilities function in human gait and running and jumping activities. The prosthetic foot of the present invention has been made in light of these scientific studies with a view toward providing an improved prosthetic foot that mimics the human foot in function in order to provide the amputee with normal human gait characteristics and improve the quality of life of the amputee.

A prosthetic foot according to the present invention comprises a forefoot portion, a midfoot portion and a hindfoot portion, wherein the hindfoot portion includes first and second joints permitting closed kinetic chain motion of the prosthetic foot in gait. The first joint has a joint axis oriented for permitting motion of the hindfoot portion about the first joint axis which is at least primarily in the sagittal plane. The second joint has a joint axis oriented for permitting motion of the hindfoot portion about the second joint axis which is at least primarily in the frontal and transverse planes. In the disclosed example embodiments, the first and second joints are formed integrally with the hindfoot portion by respective struts of resilient material of the hindfoot portion. More particularly, in one example embodiment the forefoot, midfoot and hindfoot portions of the prosthetic foot are formed of a single piece of plastic as by molding and/or machining.

In a second embodiment, the improved prosthetic foot of the invention is formed by use of an ankle pylon component of the invention which is attached to an existing low profile prosthetic foot as a functional upgrade. The ankle pylon component contains the first and second joints which form part of the hindfoot portion of the foot. In both embodiments, the first joint in the hindfoot portion mimics an ankle joint and the second joint mimics a subtalar joint to allow the foot to function like a normal foot.

The subtalar joint in the hindfoot portion of the disclosed embodiments constitutes a means for permitting triplanar closed kinetic chain motion of the prosthetic foot in gait. This triplanar motion capability improves the foot staying plantar grade during the stance phase of gait. It also decreases residual limb to socket shear forces associated with motion in the transverse plane.

These and other objects, features and advantages of the present invention will become more apparent from the following detailed description of the disclosed, example embodiments, taken with the accompanying drawings.

BRIEF DESCRIPTION OF DRAWINGS

The foregoing and a better understanding of the present invention will become apparent from the following detailed description of the example embodiments and the claims when read in connection with the accompanying drawings, all forming a part of the disclosure of this invention. While the foregoing and following written and illustrated disclosure focuses on several example embodiments of the invention, it should be clearly understood that the same is by way of illustration and example only and the invention is not limited thereto. The spirit and scope of the present invention are limited only by the terms of the appended claims.

The following represents brief descriptions of the drawings, wherein:

FIG. 13 is a cross-sectional view through a lower portion of the midfoot portion of the body of the prosthetic foot taken along the line XIII—XIII in FIG. 2 showing the inclination of the longitudinal arch at angle ε with the transverse plane with the medial more proximal than the lateral.

FIG. 14 is a side view of an integrally formed metal attachment device for the prosthetic foot.

FIG. 15 is a top view of the device in FIG. 14.

FIG. 16 is a top view of the lower attachment plate of the device of FIG. 14.

DETAILED DESCRIPTION OF DISCLOSED EMBODIMENTS

Figure 2:
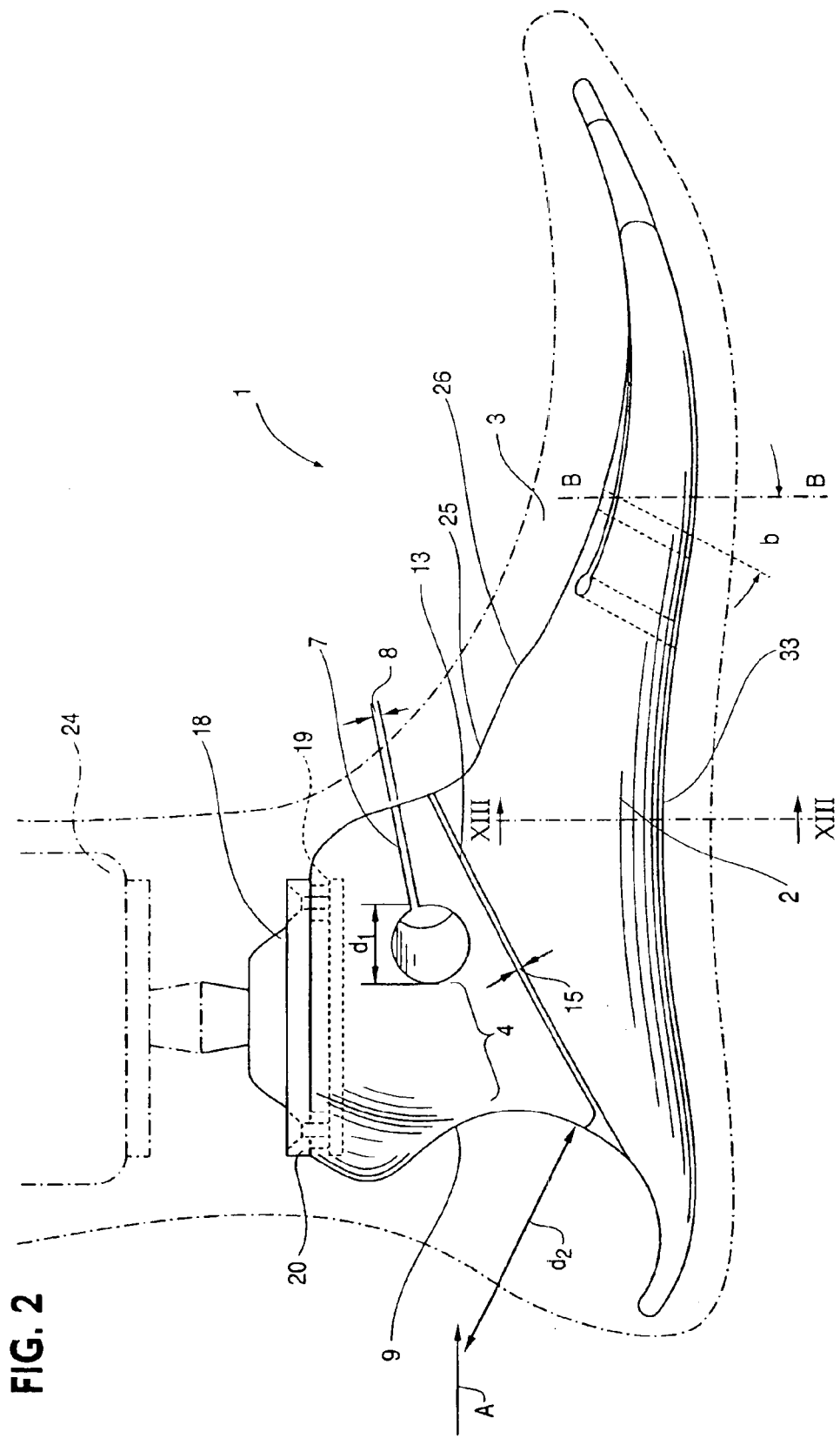
FIG. 2 is a lateral side view of the prosthetic foot of FIG. 1 located within a cosmetic covering of the foot, shown in dashed lines, and in position for connection with an adjoining prosthesis on the amputee's leg, also shown in dashed lines.

Referring now to the drawings, a prosthetic foot 1 of a first example embodiment of the invention comprises a body 2 formed of a resilient, semi-rigid material, plastic in the disclosed embodiment, which is formed with forefoot, midfoot and hindfoot portions 2A, 2B and 2C, respectively. A cosmetic covering 3 of the foot surrounds the body 2 as depicted in FIG. 2. The body 2 in the disclosed embodiment is formed by molding or by pouring the material of the body into a negative mold. However, other processes could be employed to form the body 2 such as machining the body from a solid piece of resilient, semi-rigid material, or by using a combination of molding and machining, for example. The plastic of body 2 is an elastomer, polyurethane in the illustrated example but other plastics or composite materials could be used. The body 2 of the foot is shaped and designed to simulate a human foot's hindfoot triplanar, forefoot biplanar and hindfoot, midfoot and forefoot dynamic response windless effect motion capabilities as discussed herein.

Figure 6:
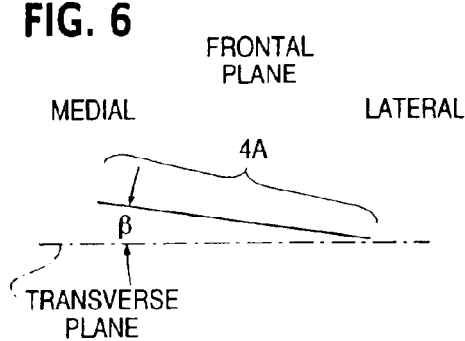
FIG. 6 is a schematic view of the ankle joint axis of the prosthetic foot as projected on the frontal plane wherein it is seen that the ankle joint axis is deviated from the transverse plane by an angle $\beta$ with the medial more proximal than the lateral.

The rear foot triplanar motion capability is achieved by the hindfoot portion 2C which includes first and second joints 4 and 5 permitting closed kinetic chain motion of the prosthetic foot in gait. The first joint 4 acts as an ankle joint. The second joint 5 acts as a subtalar joint. The ankle joint axis of rotation 4A is oriented for permitting motion of the hindfoot portion 2C about the joint axis 4A which is at least primarily in the sagittal plane. More particularly, the ankle joint axis 4A is preferably externally rotated an angle α of 8° to 30° from a line drawn normal to the long axis X—X of the foot, see FIG. 4. The ankle joint axis 4A also deviates from the transverse plane an angle β of 8° with the medial more proximal than the lateral, see FIG. 6. This ankle joint axis of rotation orientation allows the prosthetic foot to mimic human foot ankle joint sagittal and frontal plane motion capabilities.

Motion in the open chain cannot occur in the prosthetic foot because of the lack of muscular control. However, in closed kinetic chain motion, dorsiflexion with abduction appears as forward movement of the leg on the foot with internal rotation of the leg. Plantar flexion with adduction appears as backward movement of the leg on the foot with external rotation of the leg. Ground reaction forces create these motions by way of the prosthetic foot 1.

The ankle joint 4 and subtalar joint 5 are formed integrally with the hindfoot portion 2C by respective struts 4B and 5B of the resilient material of the hindfoot portion. The struts are each elongated in the direction of their respective joint axis. The anterior and posterior side surfaces of the ankle joint strut 4B and the medial and lateral side surfaces of the subtalar joint strut 5B are concavely curved for transferring and absorbing forces in motion of the hindfoot portion about the ankle and subtalar joint axes. The concavely curved anterior side surface of the strut 4B is formed by the periphery of a hole 6 which extends through the hindfoot portion 2C along the anterior side of the strut 4B. The diameter $d_1$ of hole 6 in foot 1 is ⅝ inch but this can vary dependent upon the overall size of the body 2 of the foot 1.

Anterior to the hole 6 is a gap 7 which permits the motion of the hindfoot portion 2C about the joint axis 4A. The height 8 of gap 7 is selected so that a lower surface of the body 2 adjacent the gap 7 acts as a stop against an opposing upper surface defining the gap to limit the amount of motion of the hindfoot portion 2C about the ankle joint axis 4A in dorsiflexion. The wider the anterior gap, the more potential for dorsiflexion range of motion. The hole 6 in the illustrated embodiment extends in a direction parallel to the joint axis 4A.

Figure 7:
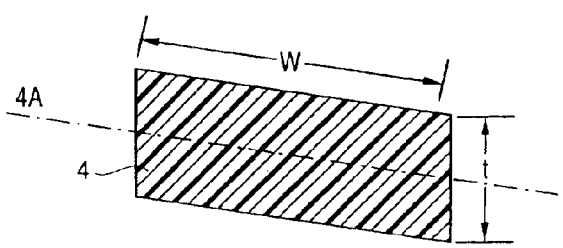
FIG. 7 is a cross-sectional view of the ankle joint strut taken along the section VII—VII in FIG. 3.

The posterior aspect of the ankle joint strut 4B of the hindfoot portion 2C is a concavity having a diameter $d_2$ of 1½–2 inches in the example embodiment but this can vary and is determined by the overall size of the body 2. For example, for an infant or small child's foot the diameter $d_2$ would be smaller. The proximal aspect of concavity 9 preferably extends in a direction parallel to the ankle joint axis 4A. The distal aspect of concavity 9 can extend in a direction parallel to the ankle joint axis 4A or extends in a direction parallel to the frontal plane. This curvature is necessary to absorb shock and to allow freer plantarflexion range of motion about the ankle joint. To create ankle joint motion capability, the width w and thickness t of the plastic ankle strut 4B, see FIG. 7, can be varied as can the density, durometer and other properties of the material utilized. For example, an above the knee prosthetic foot needs different motion characteristics than a below the knee prosthetic foot.

Figure 8:
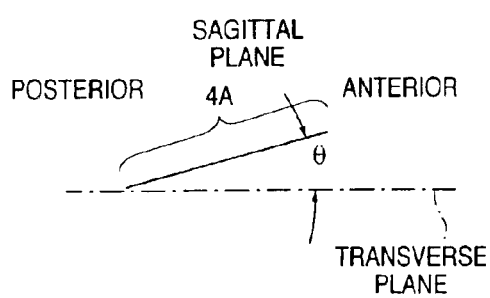
FIG. 8 is a schematic view of the ankle joint axis of the prosthetic foot as projected on the sagittal plane wherein it is seen that the ankle joint axis is deviated from the transverse plane by an angle $\theta$ with the anterior more proximal than the posterior.

It is well understood in the prosthetic profession that a heel lever creates flexion torque and that a toe lever creates extension torque. As a consequence, the motion requirements are different for above the knee and below the knee prosthetic feet. As a result, an above the knee prosthetic foot may have a different posterior ankle joint concavity radius of curvature and it may be formed of a less dense material. This in effect, would decrease the heel lever and the resultant flexion torque associated with it. The ankle joint axis 4A as projected on a sagittal plane is inclined from the transverse plane an angle θ with the anterior being more proximal than the posterior, see FIG. 8. The angle θ in the enclosed embodiment is the same as the angle β in FIG. 6, 8°.

Figure 1:
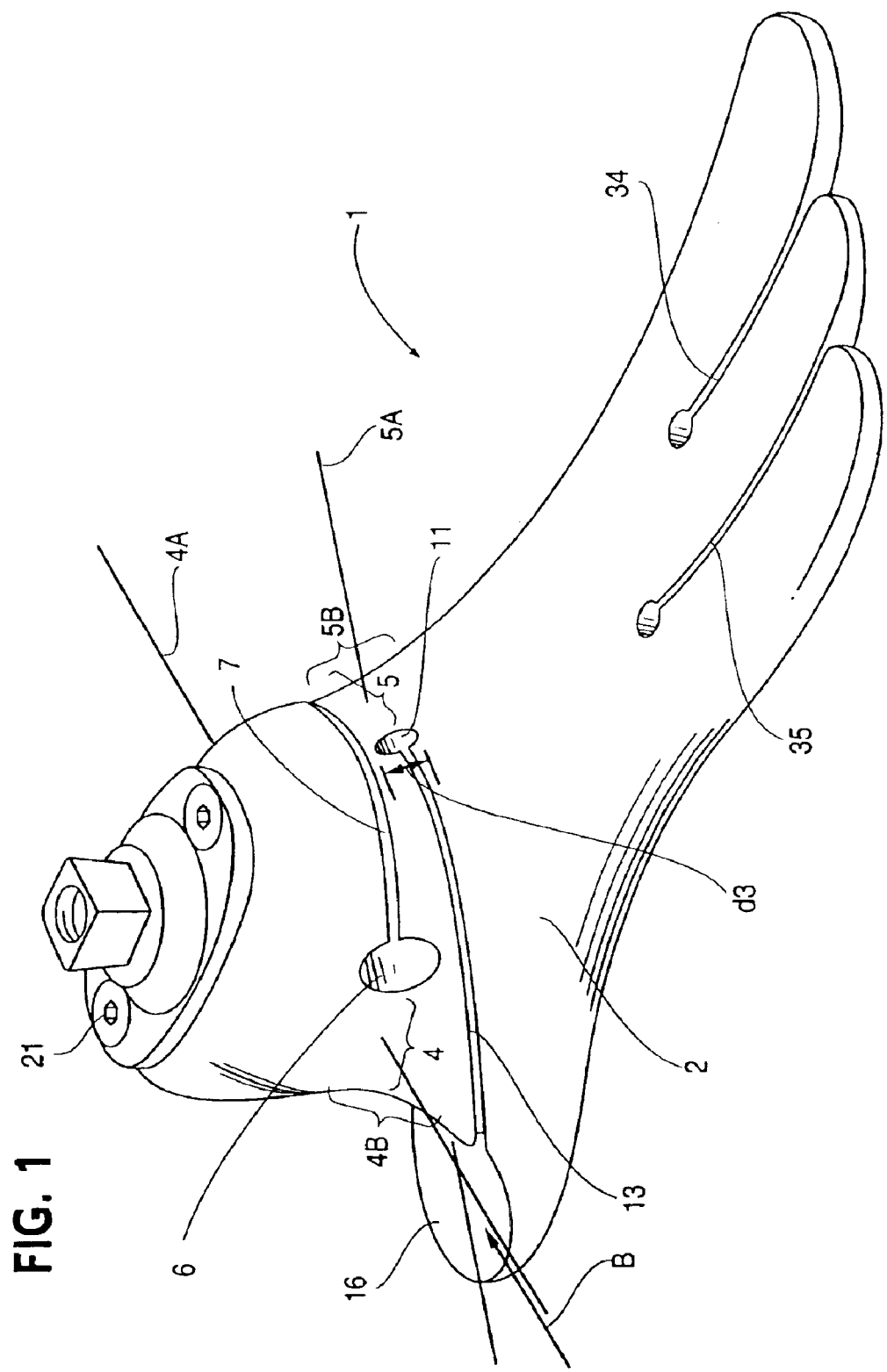
FIG. 1 is a perspective view, from the right front and slightly above, of a right prosthetic foot according to a first example embodiment of the invention.
Figure 9:
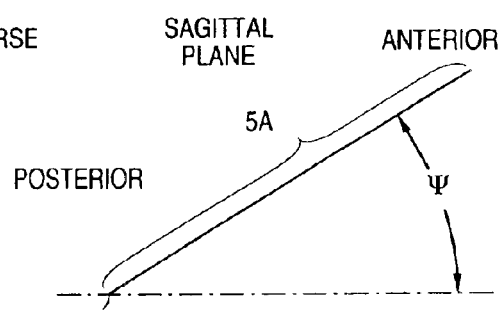
FIG. 9 is a schematic view of the subtalar joint axis of the prosthetic foot as projected on the sagittal plane showing the subtalar joint axis making an angle ψ with the transverse plane with the anterior more proximal than the posterior.

The subtalar joint 5 in the prosthetic foot 1 is spaced below and extends in a different direction than the ankle joint 4. The subtalar joint axis 5A extends along the subtalar joint strut 5B and is oriented for permitting motion of the hindfoot portion 2C about the joint axis 5A in all three of the frontal, transverse and sagittal planes, although primarily in the frontal and transverse planes. The joint axis 5A runs in the hindfoot portion 2C from posterior, plantar and lateral to anterior, dorsal and medial. Preferably, the joint axis 5A as projected on a transverse plane is inclined at an angle $\Delta_1$ of 9° to 23° with the longitudinal axis of the foot, X—X in FIG. 4. The angle $\Delta 1$ is 23° in the example embodiment. The joint axis 5A as projected on a sagittal plane (the oblique axis of joint 5), as seen in the direction of arrow B in FIG. 1, makes an angle ψ of 29° to 45° with respect to the transverse plane, see FIG. 9. The angle ψ is 30° in the disclosed embodiment.

Figure 10:
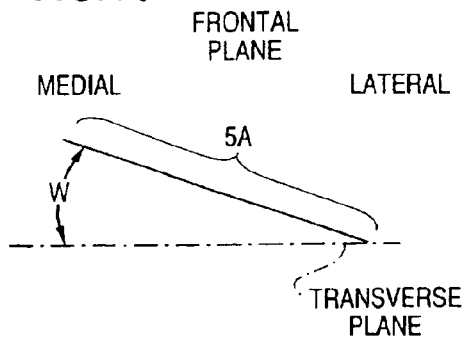
FIG. 10 is a schematic view of the subtalar joint of the prosthetic foot as projected on the frontal plane with the axis making an angle ω with the transverse plane with the medial more proximal than the lateral.

The subtalar joint 5 is bounded medially and laterally by respective holes 10 and 11 which extend parallel to the joint axis 5A. The diameter $d_3$ of the holes is variable depending on the overall size of the body 2. It is 3/16 inch in the example embodiment. Medial and lateral gaps 12 and 13 extend along the subtalar joint outwardly from the holes 10 and 11, respectively, to the periphery of the body 2 of the foot to permit the motion of the hindfoot portion 2C about the subtalar joint axis 5A. The height 14 of the medial gap 12 and the height 15 of the lateral gap 13 are selected so that a lower surface of the hindfoot portion 2C defining each gap acts as a stop against the opposing upper surface defining the gap to limit the amount of bending or rotational motion of the hindfoot portion about the joint axis 5A in eversion and inversion in gait. The height of the medial gap 14 is preferably greater than, such as twice that of the lateral gap 15. The height 14 is ⅛ inch and height 15 is 1/16 inch in the example embodiment. The joint axis 5A as projected on the frontal plane, as seen in the direction of arrow A in FIG. 2, is inclined an angle W to the transverse plane with the medial being more proximal than the lateral, see FIG. 10.

The subtalar joint axis of rotation 5A in the prosthetic foot 1 mimics the human foot's subtalar joint in function. The significance of the longitudinal axis of rotation 5A of the joint 5 being oriented externally 9–23° from the long axis of the foot is in allowing medial and lateral or frontal plane motion capability. The amount of possible frontal plane motion of the prosthetic foot at the joint 5 is dictated by the height of the medial and lateral subtalar joint gaps 14 and 15. Since the human foot typically has 20° inversion and 10° eversion range of motion capability about the human foot subtalar joint, the medial gap 14 of prosthetic foot 1 is, as noted above, preferably twice as wide as the lateral gap 15 to allow a greater range of inversion than eversion.

The curvature on the medial and lateral sides of the strut 5B provided by the holes 10 and 11 prevents the plastic from breaking by reducing stress concentration. The subtalar joint's oblique axis of rotation, FIG. 9, allows the joint to act as a mitered hinge. A simple torque converter has been created and rotation of the leg or vertical segment connected to the foot 1 will result in near equal rotation (in the case ψ is 45° of the horizontal segment. This orientation will improve transverse and frontal plane motion capability. When the angle ψ of the oblique axis of the subtalar joint 5 is 30° instead of 45°, the axis is twice as close to the horizontal plane as to the vertical plane and twice as much motion of the foot occurs in the frontal plane as in the transverse plane with a given rotation of the leg about its longitudinal axis. The importance of transverse plane motion capability at the subtalar joint 5 is for transverse plane torque absorption, for reduction of shear forces at the residual limb to socket interface and for avoiding the need to add a separate torque absorber to the prosthetic foot.

The average transverse plane rotation of the lower leg of a person in gait is 19°. The subtalar joint is the mechanism in the human foot, and also in the prosthetic foot 1, which allows these 19° of rotation to occur. Closed kinetic chain motion of the subtalar joint 5 in the foot 1 remains inversion with supination and eversion with pronation in the frontal plane. The subtalar joint functional range of motion in gait is 6° total motion. In the case only 6° of frontal plane motion is needed in the prosthetic foot 1, it is possible to incline the oblique axis of the joint 5 toward the upper end of the range 30°–45° to derive a comfort benefit.

Figure 3:
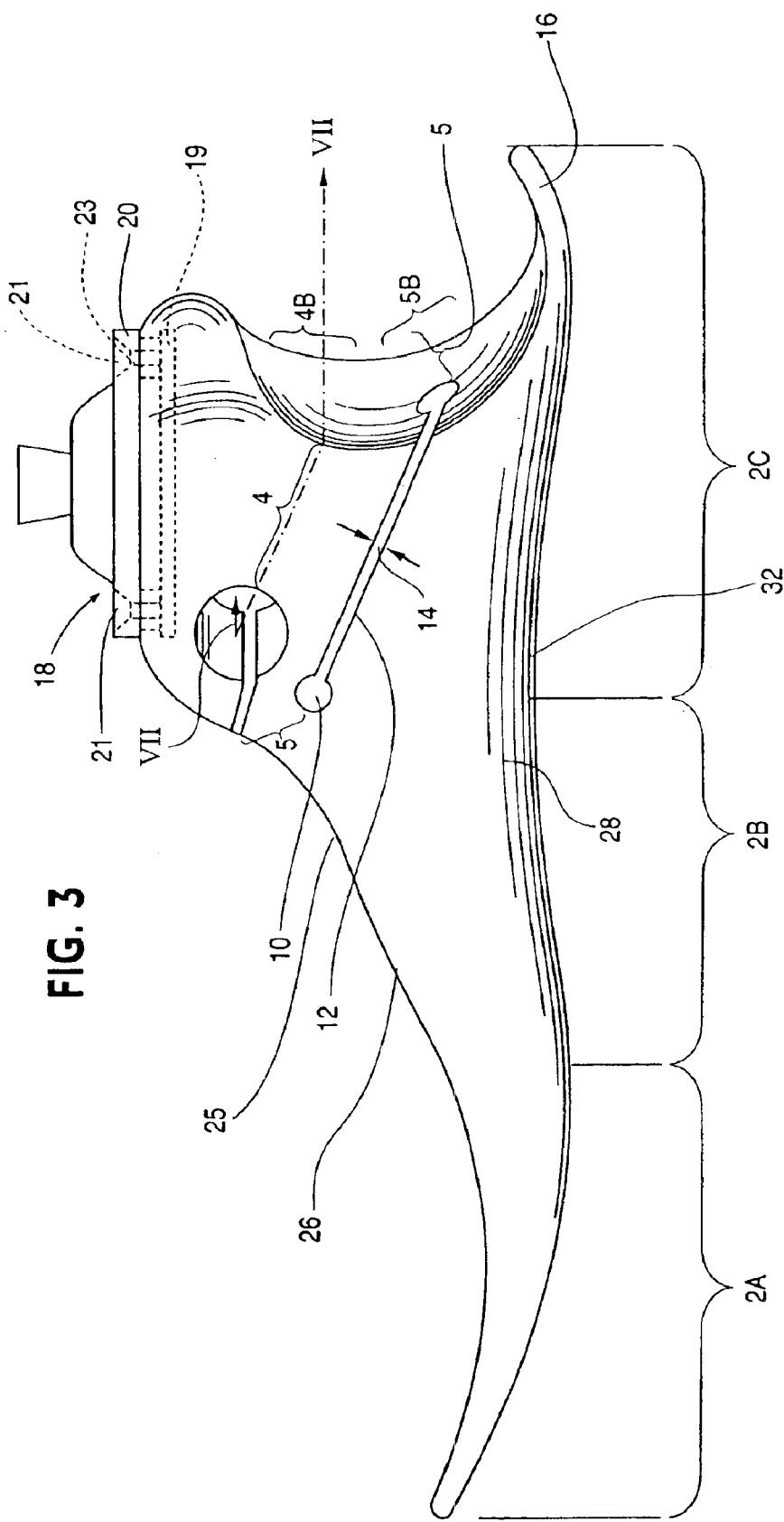
FIG. 3 is a medial side view of the prosthetic foot of FIG. 1.
Figure 4:
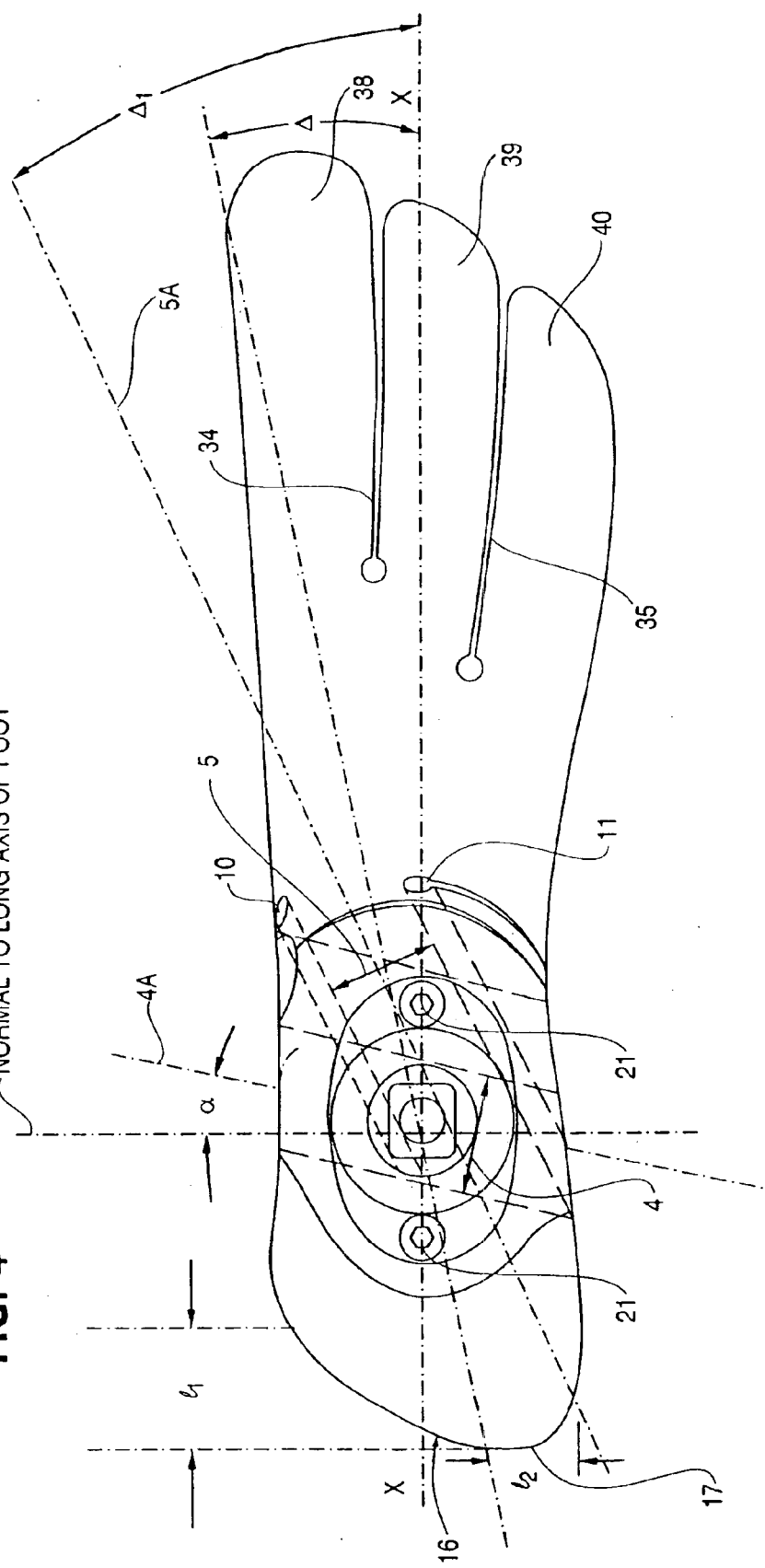
FIG. 4 is a top view of the prosthetic foot of FIG. 1.
Figure 5:
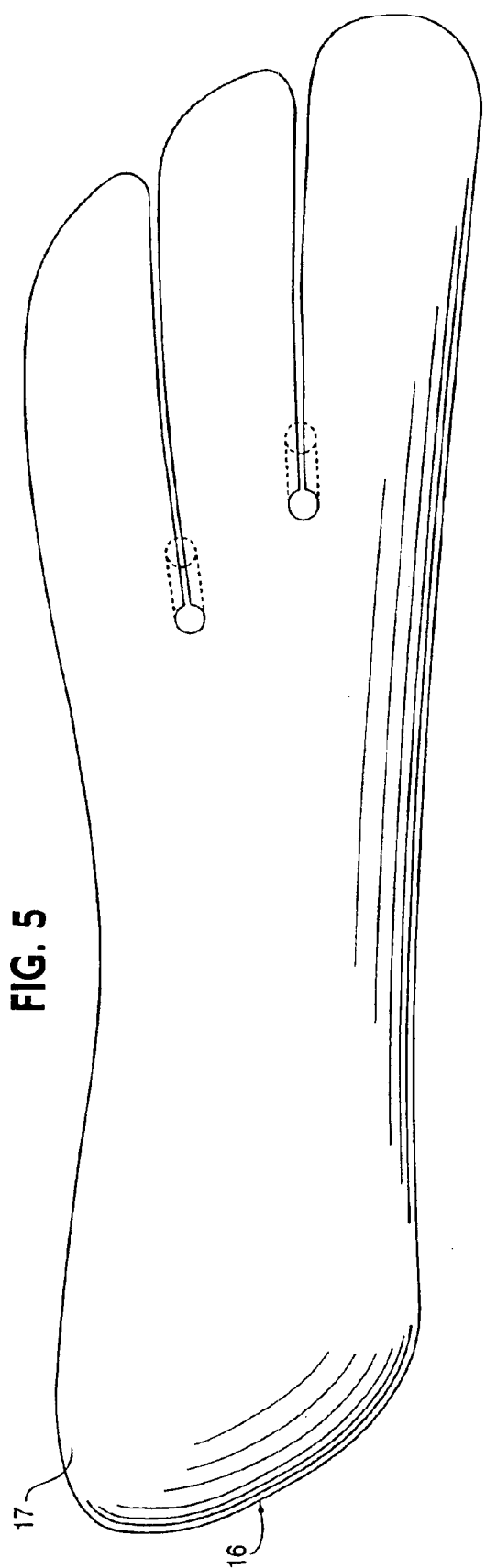
FIG. 5 is a bottom view of the prosthetic foot of FIG. 1.

The hindfoot portion 2C of the foot 1 is also formed with a heel 16 with a posterior lateral corner 17 which is more posterior and lateral than the medial corner of the heel to encourage hindfoot eversion during the initial contact phase of gait. As shown in FIGS. 4 and 5, the posterior aspect of the heel 16 is a duck-tail shaped torsion bar with the lateral posterior corner 17 thereof offset a distance $l_1$ of ½ to ¾ inch more posterior than the medial corner. The use of a smaller angle Δ of 16°, for example, or a more medial positioning of the subtalar joint strut 5B as discussed later also causes the heel corner 17 to be offset a distance of $l_2$ of ½ inch more lateral than the projected axis of the subtalar joint. This ½ inch lateral offset predisposes the rear foot at heel strike to cause the subtalar joint to evert. This initial contact subtalar joint eversion acts as a shock absorber to dampen the impact of the heel strike. In addition, the shape of the posterior lateral corner of the foot in the sagittal plane is curved upwardly, see FIGS. 2 and 3, with a radius of curvature of 1½ to 3 inches in the disclosed embodiment. This radius of the curvature can vary depending on the overall size of the foot. This large radius of curvature allows the posterior lateral corner to deflect proximally at heel strike which also acts as a shock absorber. The density of plastic in the posterior aspect of the body 2 of the foot 1 could also be selected to be less than that in the rest of the body of the foot to create even more shock absorption capability.

The top 23 of the hindfoot portion 2C of the prosthetic foot 1 is made flat and has a metal attachment device 18 embedded into the plastic. The metal device 18 is made of stainless steel in foot 1, but other high strength, light weight metal alloys, such as Ti alloys, could be used utilized. The device 18 permits attachment of the prosthetic foot to a prosthetic component 24 secured to a person's limb above the foot as schematically depicted in FIG. 2. The lower part 19 of the attachment device 18 is embedded into the material of the hindfoot portion 2C during molding. Preferably, this lower part 19 has several holes therethrough to aid in anchoring the device in the molded elastomer of body 2 at the time of molding. In the disclosed example embodiment, the attachment device comprises an upper pyramid attachment plate 20 connected in spaced relation to a lower attachment plate 19 by a plurality of fasteners 21 as shown in the drawings. Alternatively, the upper and lower attachment plates and connecting elements could be formed integrally as shown in FIG. 14. The attachment device 18 is located in the hindfoot portion 2C along the longitudinal axis X—X of the foot 1 as shown in the drawings.

The metal attachment device 18' in FIG. 14 comprises integrally formed lower attachment plate 19', upper pyramid attachment plate 20' and connecting struts 21'. The lower plate 19' is formed with an ⅛ inch proximal offset 41 on the anterior leaf and medial and lateral offsets 42 and 43, respectively. Medial and lateral holes 44 and 45 and anterior and posterior holes 46 and 47 help anchor the device in the plastic body 2 during molding. A line C—C through the holes 44 and 45 is 8° to 30° externally rotated from a normal to the sagittal plane X—X with the medial being further anterior than the lateral. The line C—C is preferably offset posteriorally a distance X' from the middle or equal orientation D—D so that the holes 44 and 45 fall in the middle of the ankle joint axis strut 4B. The posterior offset of holes 44 and 45, together with posterior hole 47 counter the toe lever length. These features can also be used on the device 18 where fasteners join separate upper and lower attachment plates 20 and 19.

Figure 11:
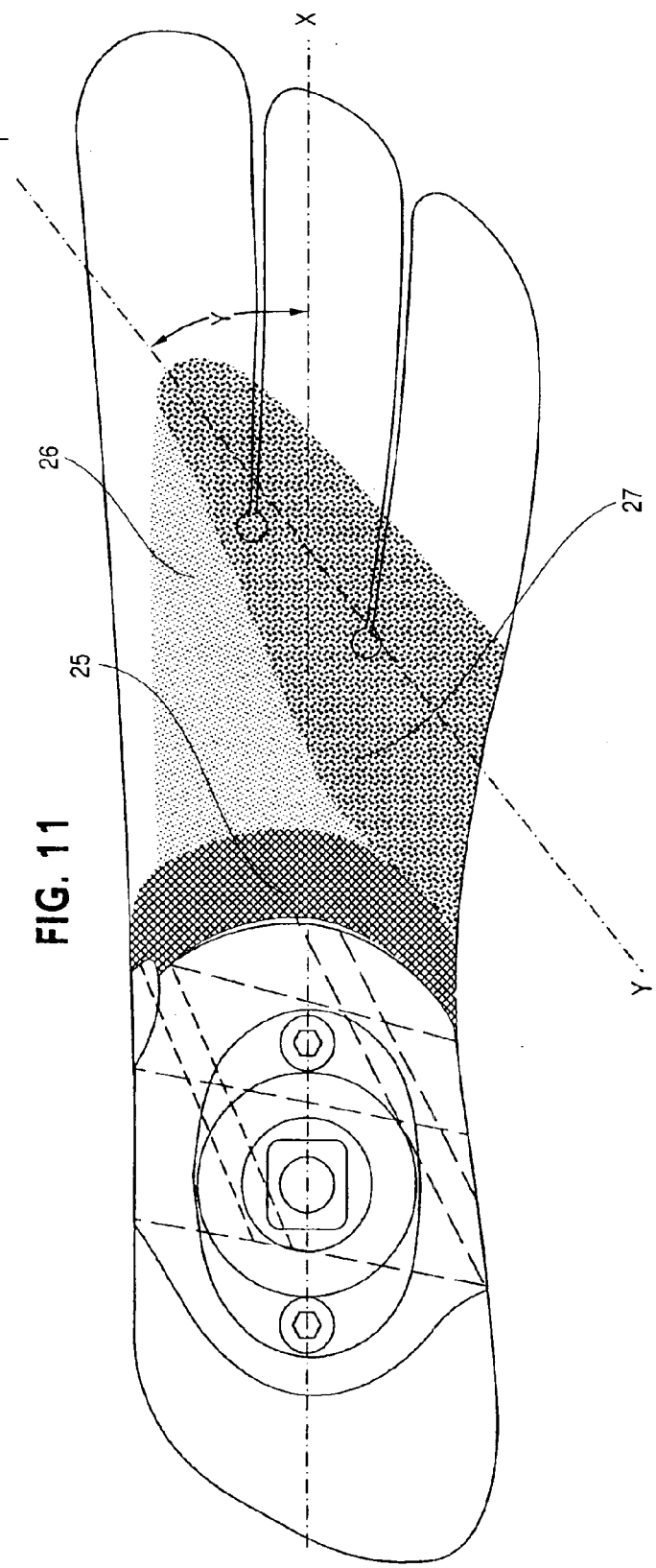
FIG. 11 is an enlarged top dorsal view of the prosthetic foot of FIG. 1 wherein shading lines have been added to show the locations of concavities and convexities on the dorsal surface of the body of the foot for effecting motion of the foot in gait.

The dorsal surface of the midfoot portion 2B anterior to the gap 7 is formed with a dorsal concavity 25 which allows the midfoot portion 2B and forefoot portion 2A to dorsiflex as weight is transferred to the anterior portions of the prosthetic foot in gait. A metatarsal arch convexity 26 is provided on the dorsal surface of the midfoot portion 2B anterior and medial from the dorsal concavity 25. In addition, the dorsal aspect of the midfoot portion 2B and forefoot portion 2A is formed with a concavity 27 which mimics in function the fifth ray axis of motion of the human foot. See the different shadings in FIG. 11 depicting the locations of concavities 25 and 27 and convexity 26 on the dorsal surface of body 2. The concavity 27 has its longitudinal axis Y—Y oriented at an angle Y of 35° to the longitudinal axis X—X of the foot with the medial being more anterior than the lateral to mimic in function the fifth ray axis of motion in gait as an oblique lower gear axis of the rotation of the second to fifth metatarsals in the human foot. The angle $\gamma$ could be less than 35°, but is preferably within the range of 15° to 35°.

Figure 12:
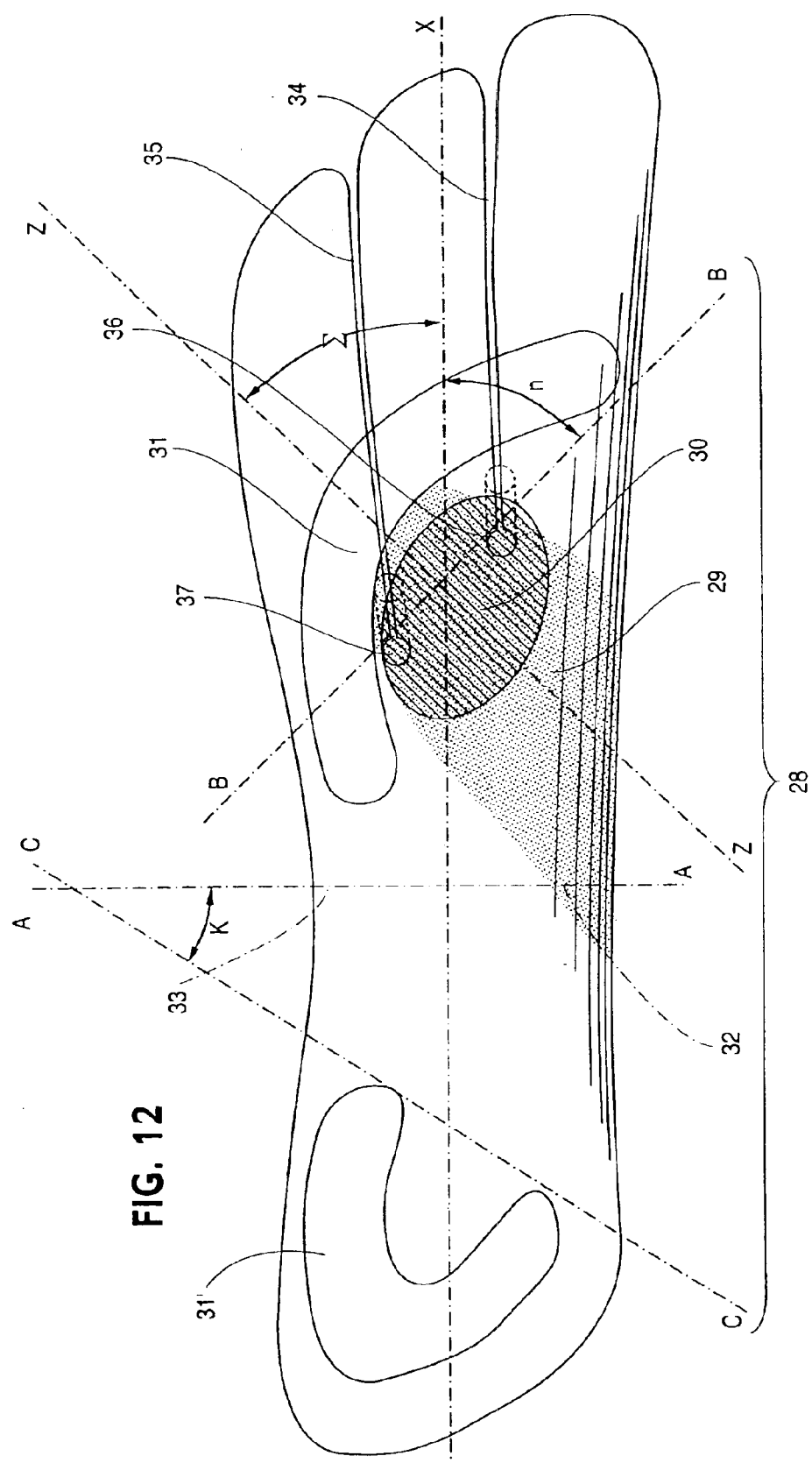
FIG. 12 is an enlarged, bottom plantar view of the body of the prosthetic foot of FIG. 1 to which lines have been added to show mid-stance contact areas of the foot on a level surface in gait and to which shading lines have been added to depict concavities on the plantar surface of the body for effecting motion of the foot in gait.
Figure 17:
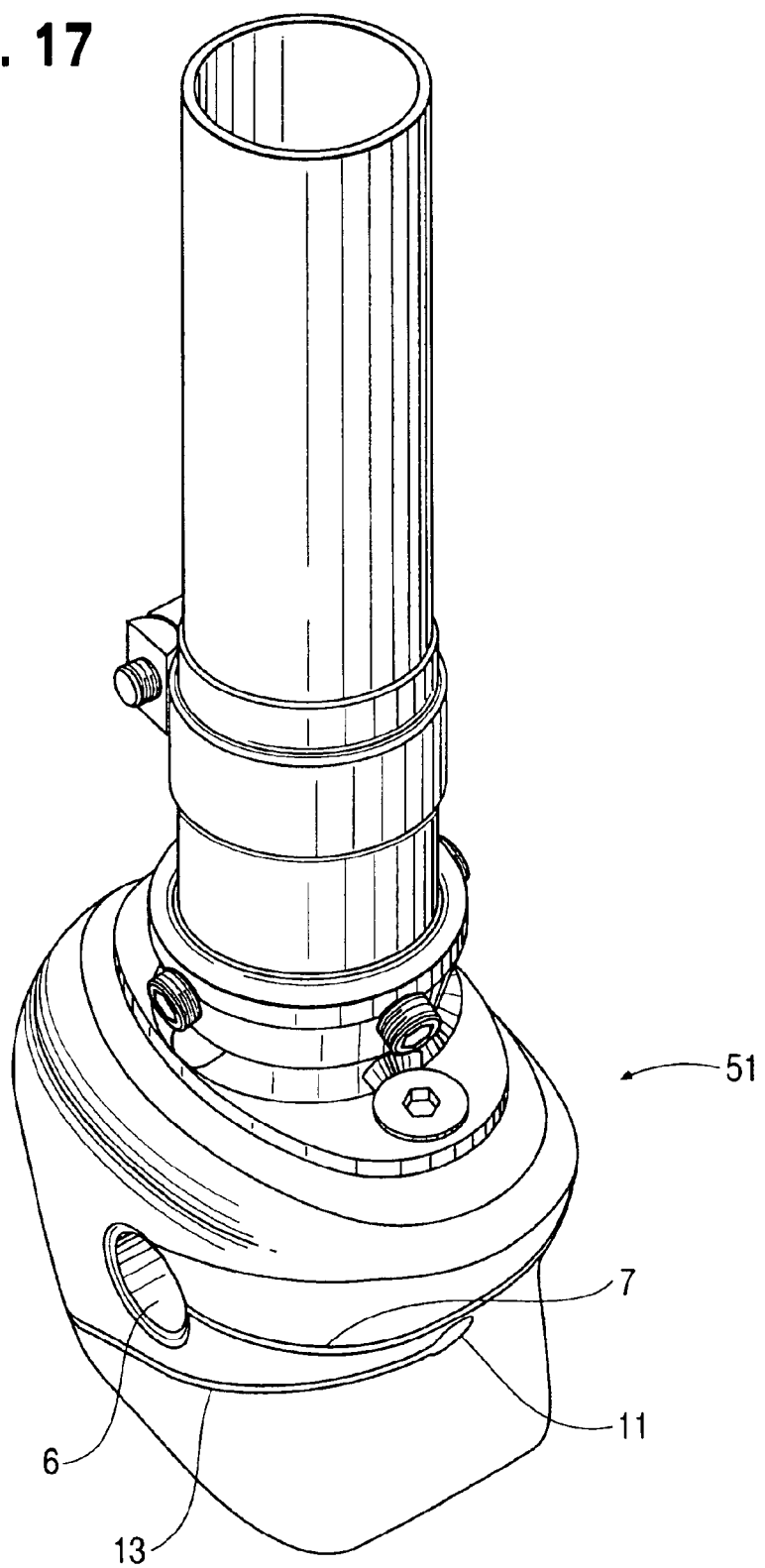
FIG. 17 is a perspective view of an ankle apparatus of the invention with a pylon attached at an upper surface thereof, the ankle apparatus being useful as an attachment to an existing low profile Seattle or similar prosthetic foot as a functional upgrade component to the foot, the combination forming another embodiment of an improved prosthetic foot according to the invention.
Figure 20:
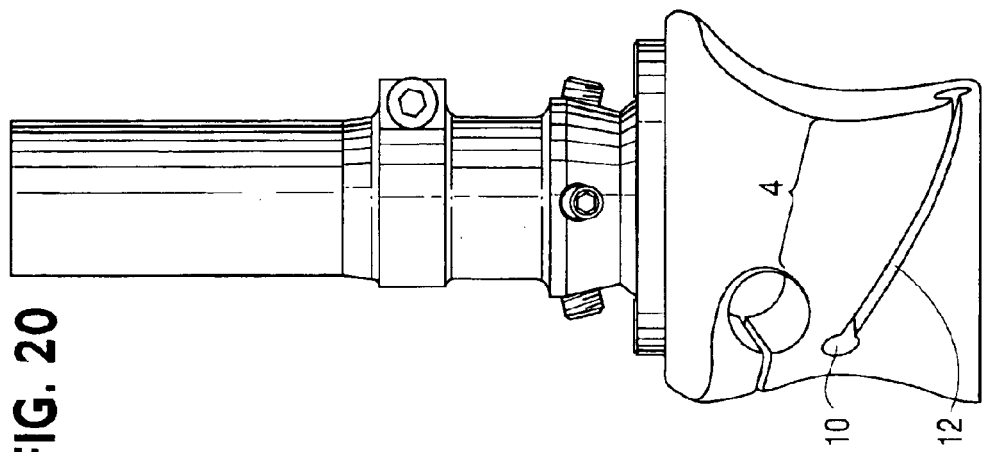
FIG. 20 is a side view of the left side of the ankle apparatus of FIG. 19.
Figure 19:
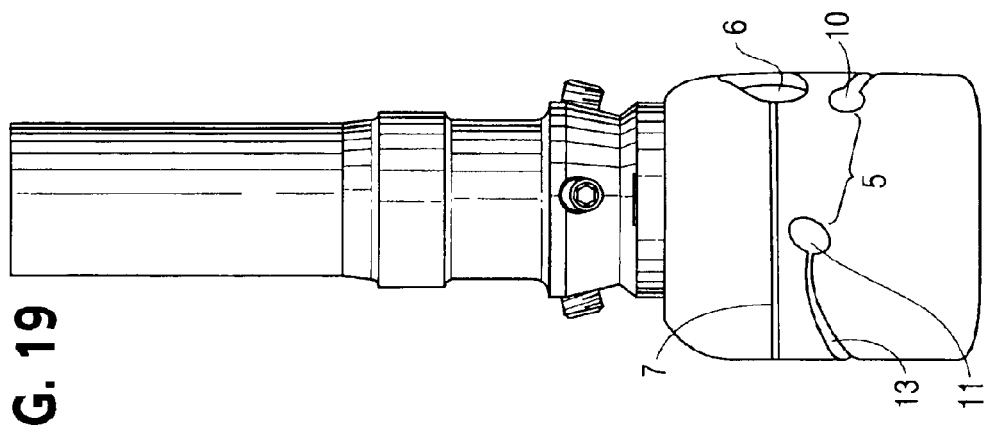
FIG. 19 is a front view of the ankle apparatus of FIG. 17.
Figure 18:
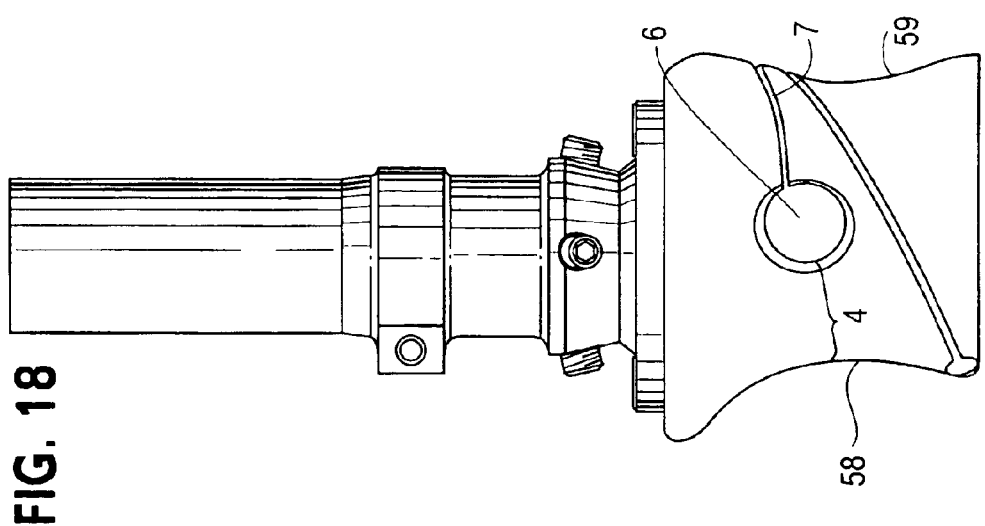
FIG. 18 is a side view of the right side of the ankle apparatus of FIG. 17.
Figure 21:
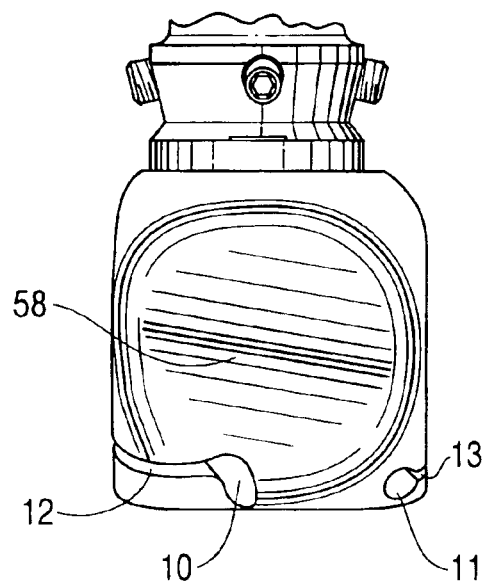
FIG. 21 is a rear view of the ankle apparatus of FIG. 17.

The plantar surface of the body 2 of foot 1 has a longitudinal arch 28, see FIG. 12, which, in the vicinity of locations corresponding to the navicular medially and the base of the fourth metatarsal laterally of the human foot, includes a concavity 29 with its longitudinal axis oriented normal to the axis Z—Z, the first ray axis of motion in the human foot to mimic the function thereof, see FIG. 12 where the concavity location is shown by shadings added to the drawing of the plantar surface of the body 2 of foot 1. The axis Z—Z in the example embodiment is at an angle $\Sigma$ of 45° to the longitudinal axis X—X of the foot with the medial more posterior than the lateral. The angle $\Sigma$ could be less than 45°, but is preferably within the range of 30° to 45°. Use of angles for $\gamma$ and $\Sigma$ at the lower end of the specified ranges will decrease the difference between the high and low gear principles. The latter may be utilized on high activity level amputees, for example. The plantar surface of the foot 1 in the anterior portion of the longitudinal arch concavity further includes a generally annular metatarsal arch concavity or cupping area 30 delineating the posterior surface of a forefoot plantar surface contact area which has been outlined at 31 as shown in FIG. 12. A hindfoot contact area is outlined at 31'.

The longitudinal arch 28 itself is formed with a concavity having a longitudinal axis A—A, FIG. 12, that as projected on the frontal plane is deviated at an angle E of 25° to 42°, see FIG. 13, with the medial higher than the lateral to create frontal and sagittal plane motion capabilities as with the midtarsal joints in the human foot. The medial aspect 32 of the longitudinal arch concavity is larger in radius and more proximal than the lateral aspect 33 of the concavity. The anterior aspect of the longitudinal arch concavity has its longitudinal axis B—B orientated at an angle η of 35° to the longitudinal axis X—X of the foot with the medial being more anterior than the lateral. The middle aspect of the longitudinal arch concavity has its longitudinal axis A—A orientation normal to the longitudinal axis X—X of the foot.

The longitudinal arch 28 is provided with this three-dimensional fan shape for causing specific motion outcomes of the foot in gait. The anterior longitudinal arch concavity blends with the first ray and metatarsal arch concavities 29 and 30. This blending of shapes causes the anterior longitudinal arch concavity to be more anteriorally and medially oriented for improving the high gear dynamic response capability of body 2. The posterior aspect of the longitudinal arch concavity has its longitudinal axis C—C deviated an angle k of 30° to the frontal plane with the medial side being more posterior than the lateral, see FIG. 12.

The midfoot portion 2B is formed of a semi-rigid material as noted above and the longitudinal arch 28 of the resilient body 2 is shaped to create a dynamic response capability of the foot in gait such that the medial aspect 32 of the longitudinal arch has a relatively higher dynamic response capability than that of the lateral aspect 33 of the longitudinal arch. As a result of this and the aforementioned features of the foot 1, biplanar motion potential exists in the midfoot portion 2B corresponding to that in the midtarsal region of the human foot where motion occurs in the frontal and sagittal planes enabling the forefoot to remain plantar grade while accommodating the positions of the rearfoot during gait. The oblique axes of the midfoot portion 2B are supinated in the propulsive phase of gait. The windless effect of the plantar aponeurosis activated with heel lift aids supination of these oblique axes during propulsion. Only 4–6° of frontal plane motion in gait is needed to keep the foot plantar grade. The prosthetic foot's physical properties, as well as its surface shapes, dictate motion potential outcomes. The longitudinal arch area of the prosthetic foot 1 is shaped specific to achieve superior functional motion outcomes. The longitudinal arch deviation from the sagittal plane as discussed above enhances the frontal plane motion and dynamic response characteristics of the foot 1.

The proximal section of the midfoot portion 2B is made flat to accept the forces of the anterior ankle joint dorsiflexion stop adjacent gap 7. The midfoot portion 2B is thicker than the forefoot portion 2A. The medial aspect 32 and 26 of the midfoot portion is thicker than the lateral aspect 33 and 27. The bottom of the foot 1 is made to accommodate ⅜ inch or ¾ inch heel heights. The plantar surface of the body 2 in the region of the forefoot and midfoot junction has the metatarsal concavity or cup area 30 as noted above. This cup area functions to create contact on the outside edges of the cup. This raised area 31 runs parallel to the axis of motion, Y—Y in FIG. 11 of the fifth ray.

The forefoot portion 2A of the body 2 has two expansion joints 34 and 35 cut into the posterior end of the forefoot. The medial expansion joint 34 runs longitudinally to just past the posterior point of ground contact on the plantar surface of the midfoot portion into the cupped recessed area 30, where it terminates in an expansion joint hole 36. The lateral expansion joint 35 runs further posterior into the forefoot than the medial expansion joint 34 where it terminates in an expansion joint hole 37. As a result, the two expansion joints function as do the high and lower gears in the human foot. As seen in FIG. 12, a straight line B-B connecting the two expansion joint holes 36 and 37 is deviated at an angle $\eta$ of 35° externally from the long axis of the foot. Since the distance from the ankle joint to the oblique axis B—B is shorter on the lateral side than the medial side, this axis is used first on heel lift before the shift to the high-gear function. The function across the high-gear or medial side, push-off results in a pronated forefoot-to-rear foot position and increased weight bearing under the medial forefoot. Thus, the forefoot portion 2A functions to allow biplanar forefoot motions to occur.

More specifically, the expansion joints 34 and 35 independently allow the forefoot to dorsiflex and invert and plantar flex and evert. This biplanar motion capability keeps the forefoot plantar grade on uneven terrain. The foot 1 mimics the human foot in this regard. As the hindfoot portion 2C changes position, the forefoot and midfoot portions need to change positions in the opposite direction. This counter twisting keeps the foot plantar grade.

The prosthetic foot 1 worn by the amputee acts as a closed chain prosthetic device which responds to the ground forces created in human gait. In the initial contact phase of gait, the posterior lateral heel strikes the ground. The design of the posterior lateral heel area is offset as discussed above to transfer weight via the duck tail shaped extension which deflects upwardly to absorb the heel lever forces which create flexion torque of the calf shank. Further enhancement of this torque absorption and improved shock absorption characteristics of the foot 1 are provided by the posterior concavity 9 and the lateral offset 12 of the heel to the axis of rotation of the subtalar joint 5 such that with force application the subtalar joint is made to evert. This eversion acts as a shock absorber to dampen the initial contact weight transfer phase of gait. In addition, force application is posterior to the axis of rotation 4A of the prosthetic ankle joint 4 causing the ankle joint to plantar flex and the midfoot and forefoot portions 2B and 2C of the foot to be lowered to the ground.

With reference to the plantar weight bearing surfaces 31 and 31' of the foot as shown in FIG. 12, as weight is transferred anteriorally from the heel portion to the forefoot portion in the entire stance phase of gait, ground reaction forces push on the plantar surface of the prosthetic foot 1. As weight is transferred through the hindfoot portion 2C, the subtalar joint 5 allows movement in the foot 1 to occur in what corresponds to the three cardinal planes of human motion, namely the transverse, frontal and sagittal planes. This triplanar motion capability is achieved because of the orientation of the prosthetic foot's subtalar joint axis of rotation 5A which is deviated from the transverse, frontal and sagittal planes as discussed above. This orientation allows motion capability in the three planes. The sagittal plane component is less than that in the frontal and transverse planes. The decreased sagittal plane motion of the subtalar joint 5 is compensated for by the ankle joint 4 which is located just proximal to the subtalar joint.

The subtalar joint's ability to allow motion to occur in the transverse plane is of significance as in the stance phase of gait, the lower extremity primarily through the subtalar joint must absorb 19° of transverse plane motion transferred through the tibia and fibula, to the ankle joint and then to the subtalar joint. The subtalar joint 5 acts as a mitered hinge and transfers this motion into the hindfoot and midfoot portions 2C and 2B. This motion is absorbed in the midfoot dynamic response qualities and in the midfoot-forefoot biplanar motion capabilities. As a result, improved plantar surface weight bearing characteristics are achieved. Before foot flat in the stance phase of gait, as the weight transfer line moves anteriorly in the foot and approaches the ankle joint 4, the ground reaction forces cause the ankle joint to plantar flex until the entire foot hits the ground. This plantar flexion motion is achieved by the ankle joint anterior gap 7 spreading or opening further and by the posterior ankle joint concavity 9 compressing.

Once the foot 1 is flat on the ground, the weight is then transferred into the ankle joint 4. As the weight transfer moves more anteriorly in the foot, the anterior dorsiflexion gap 7 engages and further dorsiflexion motion is arrested. That is, the motion is arrested by the opposing surfaces defining the anterior ankle joint gap coming together. The larger the gap 7, the more dorsiflexion motion potential. The weight transfer to the anterior ankle joint stop adjacent gap 7 is of significance. The weight is thereby transferred into the midfoot portion 2B of the foot 1. As a consequence, the area of the longitudinal arch 28 of the foot 1 is loaded and it responds with its concavity expanding and absorbing these vertical forces. The result is more shock absorption qualities and dynamic response capabilities.

The proximal medial longitudinal arch area is much larger in radius than the lateral distal. As a consequence, the medial has increased expansion potential and higher dynamic response than the distal lateral longitudinal concavity of the arch. As the weight transfer moves even more anterior in the prosthetic foot 1 approaching the medial aspect of the first ray longitudinal axis of rotation, Z—Z in FIG. 12, the weight transfer is approaching the middle frontal plane of the foot.

The plantar and dorsal surfaces of the prosthetic foot are designed to allow or encourage specific motions to occur. More specifically, the first ray axis of rotation Z—Z and the motion capability associated with this axis in the human foot are mimicked in the prosthetic foot 1 by the plantar surface of the forefoot portion 2A being shaped into the concavity 29. The longitudinal axis Z—Z of the concavity 29 is oriented to be parallel to the longitudinal axis of rotation of the first ray in the human foot. This orientation is 45° internally rotated to the long axis of the foot, see angle $\Sigma$ in FIG. 12.

The motion outcome from force application to this concavity and its degree specific orientation is vertical shock absorption and improved dynamic response capabilities. The first ray concavity 29, as well as the longitudinal arch concavity 28 create dynamic response capabilities. These dynamic response capabilities are exhibited by the ground forces transferring weight to the sides of the concavities and the concavities expanding. Thus, concavity expansion occurs in the prosthetic foot 1 during gait and once the force is removed, the foot 1 springs back into its original shape which releases stored energy.

The ankle and subtalar joints 4 and 5 in the prosthetic foot 1 also have the potential to produce a dynamic response capability. For example, as the ankle joint 4 plantar flexes and the anterior dorsiflexion gap 7 spreads and the posterior concavity 9 compresses, energy is stored in the ankle joint strut 4B. The strut 4B will return to its normal position once the vertical forces are removed.

Thus, dynamic responses of the prosthetic foot 1 in response to ground reaction forces are associated with expansion and compression of concavities and convexities and to a lesser degree with movement that occurs and the design features of a specific joint's strut. The struts 4B and 5B constitute the middle pivot points of class 1 levers in the hindfoot portion 2C. The ankle and subtalar joint struts each have energy storing capabilities. The physical properties, as well as the design characteristics, create the dynamic response capabilities. Force application will cause movement to occur. Once the force is removed, the physical properties of the strut make it return to its original resting shape and as a consequence dynamic response has occurred. While the prosthetic foot's first ray axis and fifth ray axis are not distinct joint axes, the shape and design of the surface features of the body 2 of the prosthetic foot dictate functional motion capabilities such that these specific motions are encouraged to occur as discussed above.

The interrelationship between the midfoot's plantar and dorsal shapes are significant in understanding the dynamic response capabilities that exist. In this area of the prosthetic foot 1, the medial and lateral surface shapes are shape specific and these shapes provide functional movement outcomes. In gait, the lateral dorsal fifth ray concavity 27 is compressed, allowing less resisted motion potential. This relates to a low gear principle. The medial midfoot plantar and dorsal surface areas as previously described (first ray in function) respond to force application by expanding. Expansion has increased resistance qualities and as a result dynamic response capabilities are enhanced. This enhanced dynamic response capability is associated with a high gear principle.

The high gear and low gear principles relate to gait acceleration, deceleration and speed components. The high gear improved dynamic response capabilities can be utilized in gait acceleration and deceleration phases. A low gear principle relates more to the speed of gait, rather than the aforementioned acceleration and deceleration. The low gear component of the prosthetic foot 1 will allow the amputee to ambulate with less energy expenditure while walking at slower speeds. This decrease in energy expenditure is associated with two principles, namely the length of the toe levers as these toe lever lengths relate to extension torque of the calf shank, and to the dynamic response characteristics of the medial and lateral areas of the prosthetic foot.

The high gear has a longer toe lever than the low gear. When the amputee walks slowly, less momentum and inertia are created. The ability to efficiently overcome a long toe lever is less. The body's center of gravity shifts more laterally during slow walking in the stance phase of gait. With the improved frontal plane motion capabilities of the prosthetic foot 1, the patient's calf shank can be positioned to move into the low or high gear sections of the midfoot and forefoot areas. If the amputee wearing the foot 1 is accelerating or decelerating, he will utilize the higher gear function once reaching a comfortable gait speed. The amputee will seek an area of the forefoot 2A which allows the comfortable gait speed to continue. The force transfer will occur more medial if the amputee wants more dynamic response characteristics or more lateral for less dynamic response characteristics. With the prosthetic foot 1, the amputee has a choice of functional movement outcomes.

Improved overall amputee gait patterns are the result of such selective control. As the weight transfer moves even further anteriorly in the prosthetic foot 1, the axis of the fifth ray is replicated by the arrangement of the two expansion joint holes 36 and 37 and by the shape and design of the plantar and dorsal surfaces of the body 2 of the foot. That is, the dorsal aspect of the body 2 about the fifth ray's axis of rotation Y—Y is shaped into a concavity, 27. This concavity encourages motion to occur perpendicular to the longitudinal axis orientation Y—Y. It is known that in normal gait the calf shank, tibia and fibula do not progress solely in the sagittal plane. It is known that at midstance, the knee or calf shank migrates laterally and frontal plane motions also occur. This is exhibited in the human knee by the larger surface area of the medial femoral condyle.

The function of the fifth ray axis of rotation Y—Y in foot 1 is important. As weight is transferred anterior and laterally to the prosthetic foot 1, the fifth ray longitudinal axis Y—Y allows motion to occur perpendicular to its longitudinal axis orientation. Additionally, the two expansion joint holes 36 and 37 are positioned to encourage forefoot motions that are positioned on the fifth ray's longitudinal axis of rotation and, as a consequence, improved biplanar motion capabilities are created. The low gear and high gear effects referred to above are also enhanced. As a result, the prosthetic foot gait characteristics are improved and human gait is mimicked.

The biplanar forefoot qualities of the prosthetic foot 1 are enhanced by the expansion joints and expansion joint holes as referred to above. The two expansion joint holes are strategically placed to create specific motion capabilities. That is, the two holes longitudinally, as projected on the sagittal plane are oriented at angle b of 45° from the line B-B parallel to the frontal plane, see FIG. 2. This orientation acts as a mitered hinge much like the mitered hinge of the subtalar joint. Improved biplanar motion capabilities are the result.

The plantar surface weight bearing surface 31 of the forefoot portion 2A and 31' of the hindfoot portion 2C are also design and shape specific. The plantar surface expansion joint holes 36 and 37 are located in the metatarsal arch area 30. As a consequence, as weight is transferred onto the area of the foot 1 equivalent to the metatarsal heads, the weight is borne on the expansion joint struts 38, 39 and 40. As the weight-bearing surface on the plantar aspect of the foot 1 contacts the ground, weight is borne by the expansion struts, causing a suspended web effect. This allows a tremendous amount of forming ability, while maintaining the structural stability needed for a sound stable foot. With the improved biplanar forefoot motion capabilities of the prosthetic foot, human gait is improved.

As the weight transfer in gait moves even further anteriorly into the region of the expansion joint struts and ray area, the prosthetic foot 1 is shaped and designed to create specific motion outcomes. The dorsal and plantar aspects of the aforementioned region of the body 2 are shaped in an upwardly extending arch, see FIG. 2. The dorsal aspect concavity is oriented to flow into the fifth ray concavity 27. This melding of shapes, one into another, makes for a smooth transition between late stance phase and swing phase of gait. The upwardly shaped ray region functions as dorsiflexed toes in the aforementioned gait sequence.

Although the prosthetic foot of the invention has been described in connection with the first example embodiment, alternative embodiments are possible. For example, there is a spatial relationship of the height of the ankle joint in the prosthetic foot and how this height effects the potential orientation of the oblique axis of the subtalar joint strut in the foot. In the disclosed embodiment, the height of the hindfoot (plantar surface to pyramid attachment surface) is 3–3½ inches. This height could be made larger and the ankle joint's orientation moved more proximal. This alternate orientation of the ankle joint allows the oblique axis of the subtalar joint to approach and be changed from 29–30°, to an angle of 42–45°, for example. The 30° orientation in the disclosed embodiment provides increased inversion and eversion (frontal plane motion) and decreased abduction and adduction (transverse plane motion). With the alternate embodiment having an ankle joint that is positioned more proximal, a 45° oblique subtalar joint axis will allow equal transverse and frontal plane motions. The net effect of this latter orientation would be to decrease inversion/eversion frontal plane motion and increase abduction and adduction of the foot as compared with the foot of the example embodiment. This increase in abduction and adduction would be resisted by the ground reaction forces and as a consequence there would be a decrease in the inversion and eversion capabilities and an increase in transverse plane motions.

Another possible variation would be to shift the subtalar joint strut more medial in the foot 1 and thus increase the lateral offset $l_1$ in FIG. 4. This would predispose the subtalar joint to increased eversion in the initial contact phase of gait. The net effect would be improved shock absorption capabilities. Further, the two expansion joint holes sagittal plane orientation could be changed from that in the first illustrated embodiment. These holes could be deviated medially or laterally in the frontal plane. The result of a non-sagittal orientation of these two holes is expansion joints and expansion struts which move in a more medial and lateral direction. For example, if the two expansion joint holes dorsal ends were deviated laterally 20–30° from the sagittal plane, the three expansion joint struts when acted upon by the ground reaction forces are predisposed to encourage dorsiflexion and adduction. Orienting the dorsal aspect of the expansion joint holes deviated 20–30° medially from the sagittal plane would encourage dorsiflexion and abduction of the struts. In addition, it is possible to orient the two expansion joint holes so that one hole is deviated medially and the other hole is deviated laterally. For example, the lateral expansion joint hole's dorsal aspect could be deviated medially from the sagittal plane 35°. This orientation will predispose the lateral expansion joint strut to move easier into dorsiflexion and abduction—an improved low gear effect. The medial expansion joint hole's dorsal aspect could be deviated 45° laterally from the sagittal plane. This orientation would predispose the medial expansion strut to move into dorsiflexion and adduction. The net effect is to improve the motion capability of the medial expansion joint strut as its motion is related to the high gear effect.

A still further alternate embodiment of the prosthetic foot is to have a single expansion joint and expansion joint hole so that only medial and lateral expansion joint struts are formed. This would increase the stiffness of the forefoot and decrease its biplanar motion capabilities. As previously discussed, this single expansion joint hole design could be deviated from the sagittal plane as described. An expansion joint or joints could also be provided in the heel area of the foot to improve the plantar surface of the heel staying plantar grade on uneven surfaces. The ankle joint could also be moved below the subtalar joint in the prosthetic foot. This would allow an increase in the inclination of the subtalar joint without affecting the overall height of the foot—a benefit in a low profile version of the prosthetic foot.

The body 2 of the prosthetic foot 1 can also be molded as a hybrid type foot using materials of different densities and durometers in the forefoot and midfoot portions 2A and 2B as well as in the hindfoot portion 2C. The physical properties, as well as the design characteristics of the foot create its dynamic response capabilities.

Figure 23:
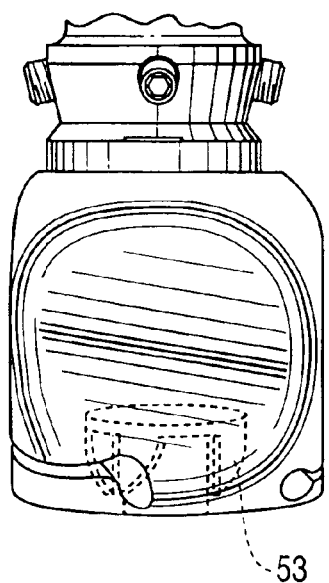
FIG. 23 is a rear view of the ankle apparatus similar to FIG. 21 but showing in dashed lines a T-shaped nut which is embedded in the resilient body of the ankle apparatus for attaching the ankle apparatus to a prosthetic foot using a threaded bolt.
Figure 22:
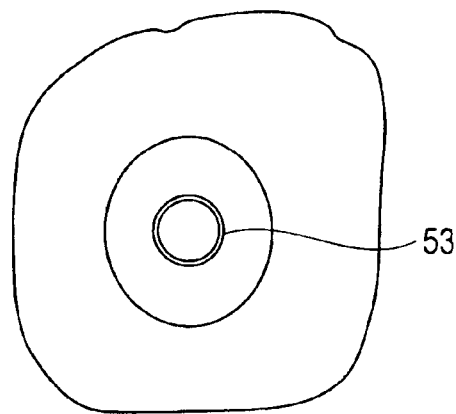
FIG. 22 is a bottom view of the ankle apparatus oriented as shown in FIG. 21.
Figure 24:
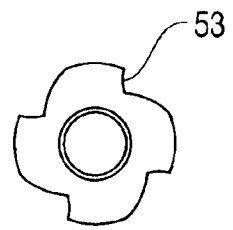
FIG. 24 is a top view of the T-shaped nut which appears in dashed lines in FIG. 23.
Figure 25:
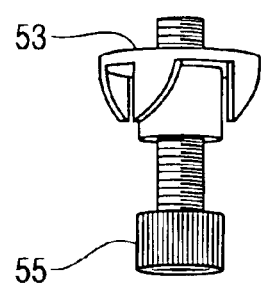
FIG. 25 is a side view of the T-shaped nut of FIG. 24 and a threaded bolt received therein.
Figure 26:
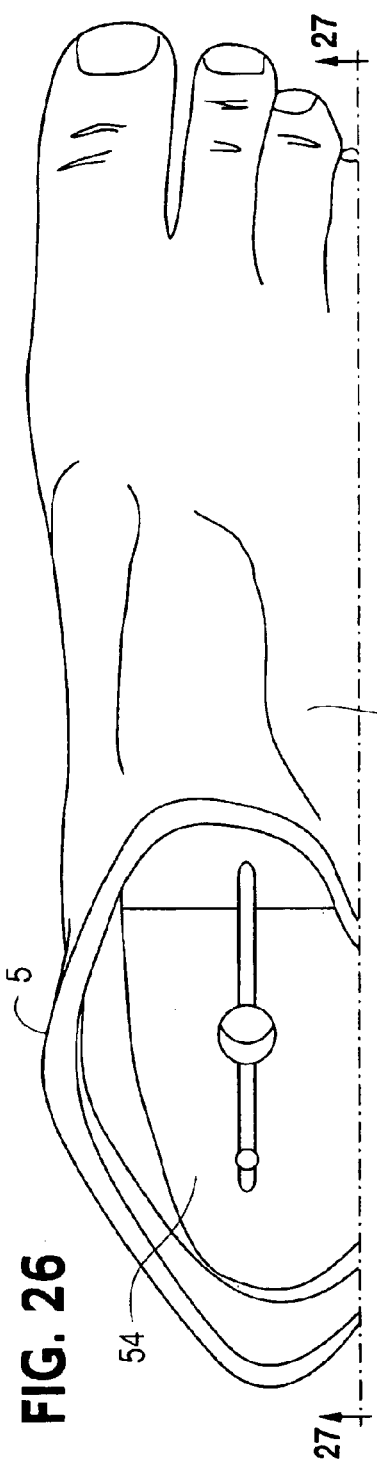
FIG. 26 is a top view of a port of a conventional low profile Seattle or similar prosthetic foot sectioned longitudinally along line XXVII—XXVII.
Figure 27:
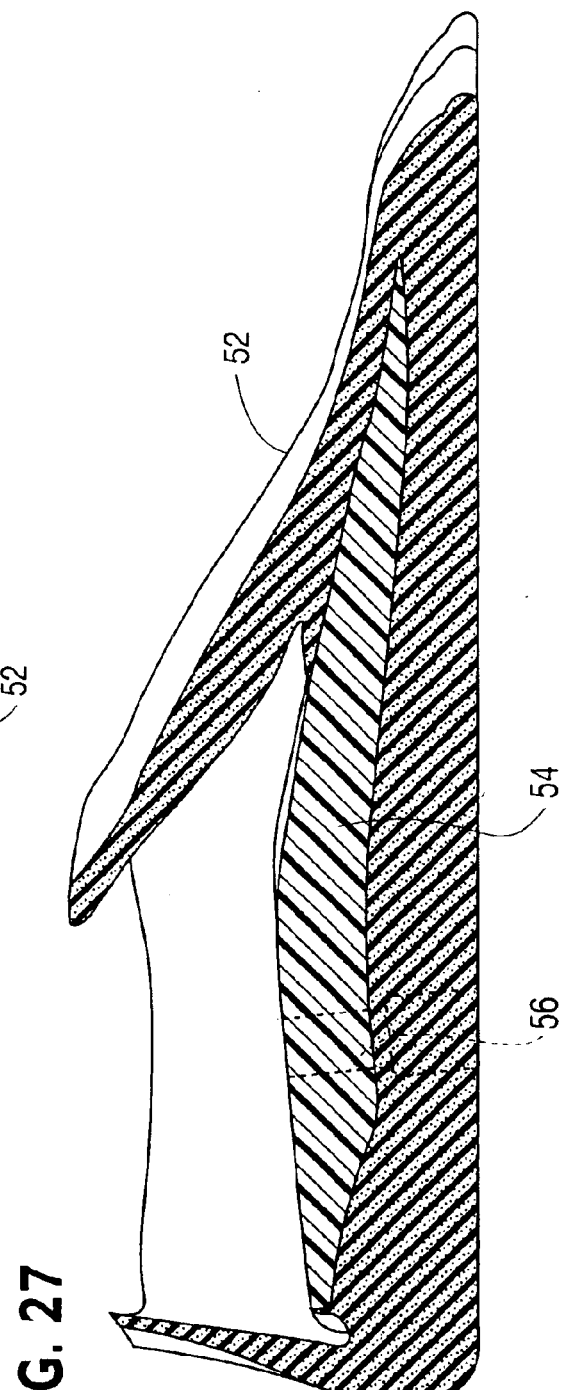
FIG. 27 is a side view of the prosthetic foot of FIG. 26.
Figure 28:
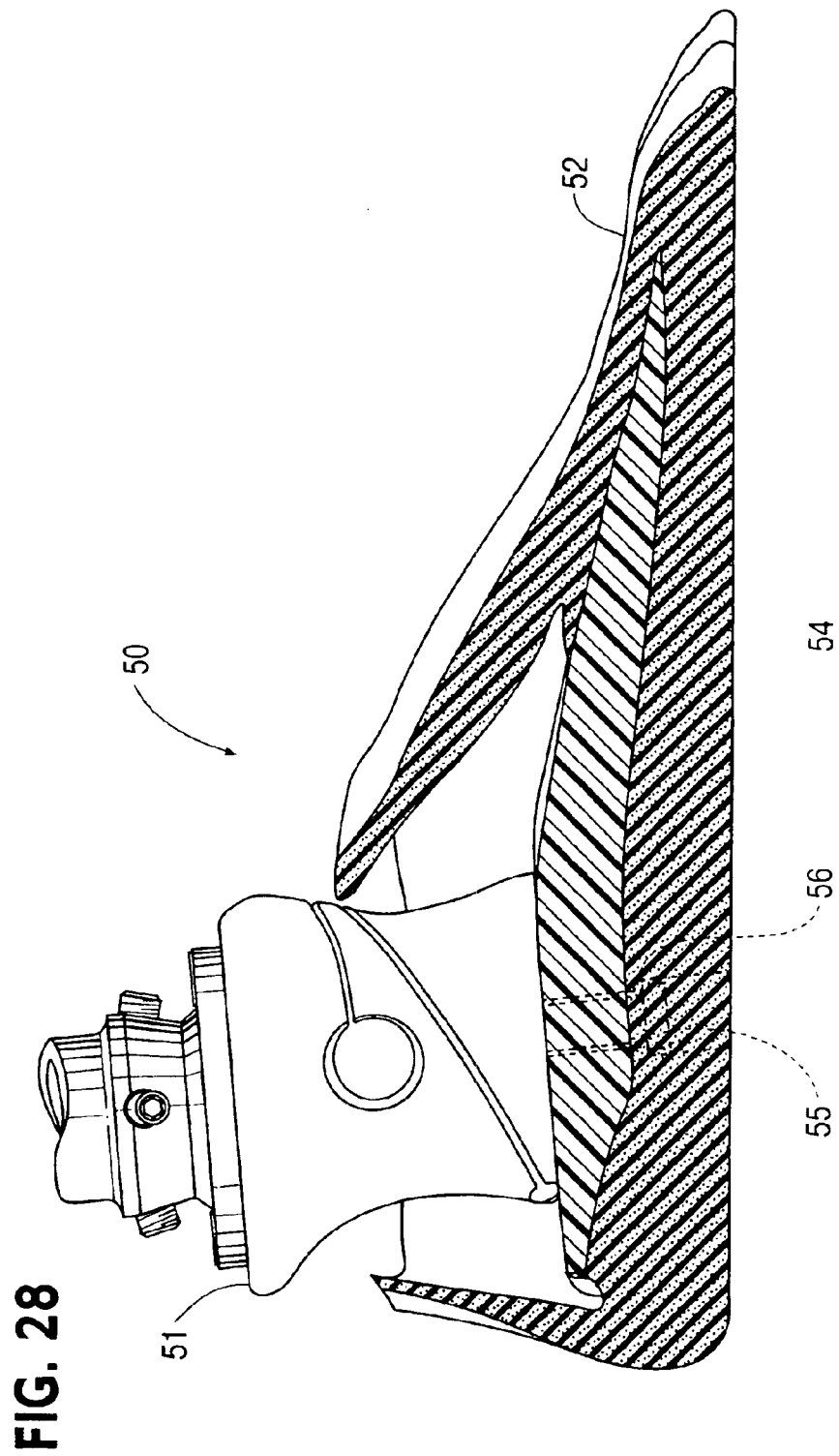
FIG. 28 is a side view of the prosthetic foot according to another embodiment of the invention.

A prosthetic foot 50 according to a second example embodiment of the invention is shown in FIG. 28. The prosthetic foot 50 comprises an ankle apparatus, e.g., an ankle pylon component, 51, according to the present invention which is attached to a conventional low profile Seattle or similar prosthetic foot 52 to improve the hindfoot functional characteristics of the foot. The ankle pylon component has a T-shaped nut 53 (see FIGS. 23–25), embedded in its distal end for attaching the component to the foot keel 54 of the foot 52 by way of a bolt 55. The bolt extends through a stepped hole 56 in the foot keel and a cosmetic covering 57 of the foot 52.

The shape and functional characteristics of the ankle pylon component are like those of the hindfoot 2C of the prosthetic foot 1 of the first example embodiment. Once attached to the top of the prosthetic foot, a posterior concavity 58 is formed. An anterior concavity 59 with smooth flowing lines is also formed as seen in the drawings. The pylon component 51 has triplanar hindfoot motion capability because of the aforementioned features described in connection with the hindfoot portion 2C of the prosthetic foot of the first example embodiment. These features include the presence of first and second joints 4 and 5 which act as ankle and subtalar joints, respectively. The T-shaped nut or similar fastener is embedded into the distal surface of the resilient plastic material of the component 51 at the time of manufacturing.

This concludes the description of the example embodiment and possible variations or alternative embodiments. However, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings, and the appended claims without departing from the spirit of the invention.

We claim:

1. A prosthetic foot comprising a forefoot portion, a midfoot portion and a hindfoot portion, said hindfoot portion including an ankle joint permitting closed kinetic chain motion of the prosthetic foot in gait, said ankle joint having a joint axis oriented for permitting motion of said hindfoot portion about said ankle joint axis which is at least primarily in the sagittal plane, said ankle joint being formed integrally with said hindfoot portion by a strut of resilient material of said hindfoot portion, wherein a hole extends through said hindfoot portion along an anterior side of said strut of said ankle joint and wherein the hindfoot portion anterior to said hole includes a gap to permit said motion of said hindfoot portion about said ankle joint axis, and wherein said joint axis as porojected on a transverse plane is 8° to 30° externally rotated with the medial side more anterior than the lateral to the long axis of the foot.

2. The prosthetic foot according to claim 1, wherein said strut is elongated in the direction of the ankle joint axis.

3. The prosthetic foot according to claim 1, wherein anterior and posterior side surfaces of said strut of said ankle joint are concavely curved for transferring and absorbing forces in motion of said hindfoot portion about said ankle joint axis.

4. The prosthetic foot according to claim 1, wherein the height of said gap is selected so that a lower surface of said hindfoot portion defining said gap acts as a stop against an opposing upper surface defining said gap to limit the amount of said motion of said hindfoot portion about said ankle joint axis in dorsiflexion.

5. The prosthetic foot according to claim 1, wherein said hole extends in a direction parallel to said joint axis of said ankle joint.

6. The prosthetic foot according to claim 1, wherein said joint axis as projected on a sagittal plane is inclined from the transverse plane with the anterior being more proximal than the posterior.

7. The prosthetic foot according to claim 6, wherein said joint axis as projected on a frontal plane is inclined from the transverse plane with the medial being more proximal than the lateral.

8. An ankle apparatus which can be attached to a prosthetic foot to form part of a hindfoot portion thereof, the ankle apparatus comprising an ankle joint which, when the ankle apparatus is attached to a prosthetic foot, permits closed kinetic chain motion of the prosthetic foot in gait, the ankle joint having a joint axis oriented for permitting motion of the hindfoot portion about the ankle joint axis which is at least primarily in the sagittal plane, wherein the ankle joint is formed by a strut of resilient material of the ankle apparatus, wherein a hole extends through said hindfoot portion along an anterior side of said strut of said ankle joint and wherein the hindfoot portion anterior to said hole includes a gap to permit said motion of said hindfoot portion about said ankle joint axis, and wherein said joint axis as projected on a transverse plane is 8° to 30° externally rotated with the medial side more anterior than the lateral to the long axis of the foot.

9. The ankle apparatus according to claim 8, wherein said strut is elongated in the direction of the ankle joint axis.

10. The ankle apparatus according to claim 8, wherein anterior and posterior side surfaces of said strut of said ankle joint are concavely curved for transferring and absorbing forces in motion of said hindfoot portion about said ankle joint axis.

11. The ankle apparatus according to claim 8, wherein the height of said gap is selected so that a lower surface of said hindfoot portion defining said gap acts as a stop against an opposing upper surface defining said gap to limit the amount of said motion of said hindfoot portion about said ankle joint axis in dorsiflexion.

12. The ankle apparatus according to claim 8, wherein said hole extends in a direction parallel to said joint axis of said ankle joint.

13. The ankle apparatus according to claim 8, wherein said joint axis as projected on a sagittal plane is inclined from the transverse plane with the anterior being more proximal than the posterior.

14. The ankle apparatus according to claim 13, wherein said joint axis as projected on a frontal plane is inclined from the transverse plane with the medial being more proximal than the lateral.

15. In a prosthetic foot comprising a foot keel extending in a longitudinal direction of the foot and a cosmetic covering about the foot keel, the improvement comprising an ankle apparatus attached to an upper surface of the foot keel to form part of a hindfoot portion of the prosthetic foot, the ankle apparatus comprising an ankle joint which permits closed kinetic chain motion of the prosthetic foot in gait, the ankle joint having a joint axis oriented for permitting motion of the hindfoot portion about the ankle joint axis which is at least primarily in the sagittal plane, wherein the ankle joint is formed by a strut of resilient material of the ankle apparatus, wherein a hole extends through said hindfoot portion along an anterior side of said strut of said ankle joint and wherein the hindfoot portion anterior to said hole includes a gap to permit said motion of said hindfoot portion about said ankle joint axis, and wherein said joint axis as projected on a transverse plane is 8° to 30° externally rotated with the medial side more anterior than the lateral to the long axis of the foot.

16. The prosthetic foot according to claim 15, wherein said strut is elongated in the direction of the ankle joint axis.

17. The prosthetic foot according to claim 15, wherein anterior and posterior side surfaces of said strut of said ankle joint are concavely curved for transferring and absorbing forces in motion of said hindfoot portion about said ankle joint axis.

18. The prosthetic foot according to claim 15 wherein the height of said gap is selected so that a lower surface of said hindfoot portion defining said gap acts as a stop against an opposing upper surface defining said gap to limit the amount of said motion of said hindfoot portion about said ankle joint axis in dorsiflexion.

19. The prosthetic foot according to claim 15, wherein said hole extends in a direction parallel to said joint axis of said ankle joint.

20. The prosthetic foot according to claim 15, wherein said joint axis as projected on a sagittal plane is inclined from the transverse plane with the anterior being more proximal than the posterior.

21. The prosthetic foot according to claim 20, wherein said joint axis as projected on a frontal plane is inclined from the transverse plane with the medial being more proximal than the lateral.

* * * * *